(12) United States Patent
Tajima

(10) Patent No.: US 12,419,599 B2
(45) Date of Patent: Sep. 23, 2025

(54) MAMMOGRAPHY APPARATUS

(71) Applicant: FUJIFILM Corporation, Tokyo (JP)

(72) Inventor: Takashi Tajima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 180 days.

(21) Appl. No.: 18/533,113

(22) Filed: Dec. 7, 2023

(65) Prior Publication Data

US 2024/0206837 A1    Jun. 27, 2024

(30) Foreign Application Priority Data

Dec. 22, 2022   (JP) .................. 2022-205935

(51) Int. Cl.
*A61B 6/50* (2024.01)
*A61B 6/04* (2006.01)
*A61B 6/42* (2024.01)

(52) U.S. Cl.
CPC ............ *A61B 6/502* (2013.01); *A61B 6/0414* (2013.01); *A61B 6/4291* (2013.01)

(58) Field of Classification Search
None
See application file for complete search history.

(56) References Cited

U.S. PATENT DOCUMENTS

| | | | | |
|---|---|---|---|---|
| 6,625,253 B1* | 9/2003 | Barnes | ............... | G21K 1/025 |
| | | | | 378/154 |
| 2002/0090055 A1* | 7/2002 | Zur | .................. | A61B 6/4291 |
| | | | | 378/154 |
| 2009/0041183 A1 | 2/2009 | Yamakita | | |
| 2014/0037058 A1* | 2/2014 | Allen | .................. | A61B 6/4441 |
| | | | | 378/62 |
| 2016/0012616 A1* | 1/2016 | Hoernig | ................. | G06T 5/70 |
| | | | | 378/37 |
| 2016/0022230 A1 | 1/2016 | Farbizio et al. | | |
| 2018/0220980 A1 | 8/2018 | Farbizio et al. | | |
| 2018/0256122 A1* | 9/2018 | Wojcik | ............... | A61B 6/4291 |
| 2019/0313989 A1 | 10/2019 | Farbizio et al. | | |
| 2020/0405248 A1 | 12/2020 | Farbizio et al. | | |
| 2021/0219933 A1* | 7/2021 | Boone | ................. | A61B 6/4447 |

(Continued)

FOREIGN PATENT DOCUMENTS

| | | | | |
|---|---|---|---|---|
| DE | 202020103638 U1 | * | 7/2020 | ........... A61B 6/0407 |
| JP | 2008-237631 A | | 10/2008 | |
| JP | 2013248091 A | * | 12/2013 | |

(Continued)

*Primary Examiner* — Marcus H Taningco
(74) *Attorney, Agent, or Firm* — Studebaker Brackett PLLC

(57) ABSTRACT

A mammography apparatus includes an imaging table, in which the imaging table is configured to attachably and detachably mount therein a scattered ray removal grid that removes scattered rays generated by the radiation transmitting through the breast, and in a case in which, in the imaging table, a direction connecting a chest wall side on which a chest wall of the subject is located and a side opposite to the chest wall is defined as a front-rear direction and a direction orthogonal to the front-rear direction is defined as a left-right direction, an opening for attaching and detaching the scattered ray removal grid is provided in the imaging table on at least any one of a left side surface or a right side surface of the imaging table.

12 Claims, 19 Drawing Sheets

(56) References Cited

U.S. PATENT DOCUMENTS

2022/0296187 A1    9/2022   Farbizio et al.
2023/0153969 A1*   5/2023   Fukuda ................ A61B 6/5217
                                                    382/130

FOREIGN PATENT DOCUMENTS

JP         2016-515877 A      6/2016
JP     WO2020194844 A1 *     10/2020

* cited by examiner

FIG. 8

| IMAGING MODE | GRID TO BE USED | DISPOSITION OF GRID | DIRECTION OF BOUNDARY LINE OF GRID |
|---|---|---|---|
| NORMAL IMAGING | BUILT-IN GRID | BUILT IN IMAGING TABLE | FRONT-REAR DIRECTION |
| BIOPSY IMAGING | INSERTION GRID | INSERTED INTO IMAGING TABLE | LEFT-RIGHT DIRECTION (MOVEMENT DIRECTION OF TUBE) |

MAMMOGRAPHY APPARATUS

CROSS-REFERENCE TO RELATED APPLICATION

This application claims priority from Japanese Patent Application No. 2022-205935, filed Dec. 22, 2022, the disclosure of which is incorporated herein by reference in its entirety.

BACKGROUND

Technical Field

The present disclosure relates to a mammography apparatus.

Related Art

JP2008-237631A describes a mammography apparatus that captures a radiation image of a breast by disposing a radiation transmission body and a radiation impermeable body that constitute a grid to extend to be substantially parallel to a chest wall of the breast, and irradiating a solid-state detector with radiation output from a radiation source through the grid.

JP2016-515877A describes an X-ray imaging device in which an anti-scattering grid having a plurality of partition walls can be configured to be positioned with respect to the X-ray imaging device such that each partition wall of the plurality of partition walls extends along a direction substantially parallel to a coronal plane of a target during imaging of the target using the X-ray imaging device. The X-ray imaging device can operate in tomosynthesis mode for imaging a chest of the target, and can include the anti-scattering grid that is disposed between a chest platform and an X-ray detector.

SUMMARY

In the mammography apparatus, in addition to normal imaging, imaging of a breast may be performed in a plurality of imaging modes, such as stereo imaging for biopsy or tomosynthesis imaging. However, a scattered ray removal grid built in an imaging table as a standard is not suitable for various imaging modes, and it is required to change the scattered ray removal grid depending on the imaging mode.

The technology of the present disclosure provides a mammography apparatus that can realize facilitation of work of changing a grid.

A first aspect according to the technology of the present disclosure relates to a mammography apparatus comprising an imaging table on which a breast of a subject is placed, which has an imaging surface on which radiation transmitted through the breast is incident, and in which a detector that detects the radiation transmitted through the imaging surface is housed, in which the imaging table is configured to attachably and detachably mount therein a scattered ray removal grid that removes scattered rays generated by the radiation transmitting through the breast, and in a case in which, in the imaging table, a direction connecting a chest wall side on which a chest wall of the subject is located and a side opposite to the chest wall is defined as a front-rear direction and a direction orthogonal to the front-rear direction is defined as a left-right direction, an opening for attaching and detaching the scattered ray removal grid is provided in the imaging table on at least any one of a left side surface or a right side surface of the imaging table.

A second aspect according to the technology of the present disclosure relates to the mammography apparatus according to the first aspect, in which the opening is provided on both the left side surface and the right side surface of the imaging table.

A third aspect according to the technology of the present disclosure relates to the mammography apparatus according to the first aspect, in which the scattered ray removal grid is a grid in which a plurality of transmission parts that transmit the radiation and a plurality of absorption parts that absorb the radiation are alternately arranged and a boundary line between the transmission part and the absorption part extends in one direction, and the scattered ray removal grid is able to be disposed inside the imaging table in a posture in which the direction in which the boundary line extends is parallel to the left-right direction.

A fourth aspect according to the technology of the present disclosure relates to the mammography apparatus according to the first aspect, in which a first fixing mechanism that fixes the scattered ray removal grid at a facing position facing a detection surface of the detector is provided inside the imaging table.

A fifth aspect according to the technology of the present disclosure relates to the mammography apparatus according to the fourth aspect, in which the first fixing mechanism includes a protrusion that is able to engage with a recess part provided in the scattered ray removal grid.

A sixth aspect according to the technology of the present disclosure relates to the mammography apparatus according to the fifth aspect, in which a support member that supports the detector and is disposed on at least a part of a periphery of the detection surface is provided inside the imaging table, and the protrusion is provided on the support member to protrude along a normal direction of the detection surface.

A seventh aspect according to the technology of the present disclosure relates to the mammography apparatus according to the sixth aspect, in which the support member is not provided on the chest wall side of the detector.

An eighth aspect according to the technology of the present disclosure relates to the mammography apparatus according to the first aspect, in which a guide part that guides the scattered ray removal grid to a facing position facing a detection surface of the detector by engaging with the scattered ray removal grid inserted from the opening is provided inside the imaging table.

A ninth aspect according to the technology of the present disclosure relates to the mammography apparatus according to the eight aspect, in which the guide part is a guide rail that is able to accept the scattered ray removal grid from the left-right direction, and the guide rail is provided outside a detection range of the radiation in the front-rear direction and the left-right direction.

A tenth aspect according to the technology of the present disclosure relates to the mammography apparatus according to the first aspect, in which a second fixing mechanism that fixes the scattered ray removal grid at a facing position facing a detection surface of the detector and is provided outside the imaging table is provided.

An eleventh aspect according to the technology of the present disclosure relates to the mammography apparatus according to the first aspect, in which the scattered ray removal grid is provided with a grip member.

A twelfth aspect according to the technology of the present disclosure relates to the mammography apparatus according to the first aspect, in which, in a case in which the scattered ray removal grid is an external grid, a built-in grid that is built in the imaging table is provided in the imaging table as a scattered ray removal grid different from the external grid, the built-in grid is movable in the imaging table between a facing position facing a detection surface of the detector and a retreat position retreating from the facing position, and the external grid is inserted into the imaging table in a state in which the built-in grid is moved to the retreat position.

The technology of the present disclosure can provide the mammography apparatus that enables the facilitation of the work of changing the grid.

BRIEF DESCRIPTION OF THE DRAWINGS

FIG. 8 is a diagram summarizing a proper use of grids in the mammography apparatus.

DETAILED DESCRIPTION

Hereinafter, embodiments of the present disclosure will be described in detail with reference to the drawings.

It should be noted that, in the following description, for convenience of description, a height direction, a width direction, and a front-rear direction (also referred to as a depth direction) of a mammography apparatus 10 are indicated by three arrows X, Y, and Z. First, the height direction is indicated by the arrow Z, an arrow Z direction indicated to by the arrow Z is an up direction of the mammography apparatus 10, and the opposite direction is a down direction. The height direction is a vertical direction. The width direction is indicated by the arrow X orthogonal to the arrow Z, a direction indicated by the arrow X is a right direction of the mammography apparatus 10, and the opposite direction is a left direction. The front-rear direction is indicated by the arrow Y as a direction orthogonal to the arrow Z and the arrow X, a direction indicated by the arrow Y is the front direction of the mammography apparatus 10, and the opposite is the rear direction. That is, in the mammography apparatus 10, a side of a stand 20 is the rear direction, and a side on which a subject A stands on the opposite side (see FIG. 2) is the front direction. In addition, in the following description, the expression using the side, such as an upper side, a lower side, a left side, a right side, a front side, and a rear side, has the same meaning as the expression using the direction.

In addition, in the present embodiment, "vertical direction" refers to the vertical direction in the sense of including an error generally allowed in the technical field to which the technology of the present disclosure belongs, that is, an error to the extent that it does not contradict the gist of the technology of the present disclosure, in addition to the exact vertical direction. In addition, similarly, "horizontal direction" refers to the horizontal direction in the sense of including an error generally allowed in the technical field to which the technology of the present disclosure belongs, that is, an error to the extent that it does not contradict the gist of the technology of the present disclosure, in addition to the exact horizontal direction.

In addition, in the present embodiment, "match" refers to the match in the sense of including an error generally allowed in the technical field to which the technology of the present disclosure belongs, that is, an error to the extent that it does not contradict the gist of the technology of the present disclosure, in addition to the exact match.

First Embodiment

Figure 1:
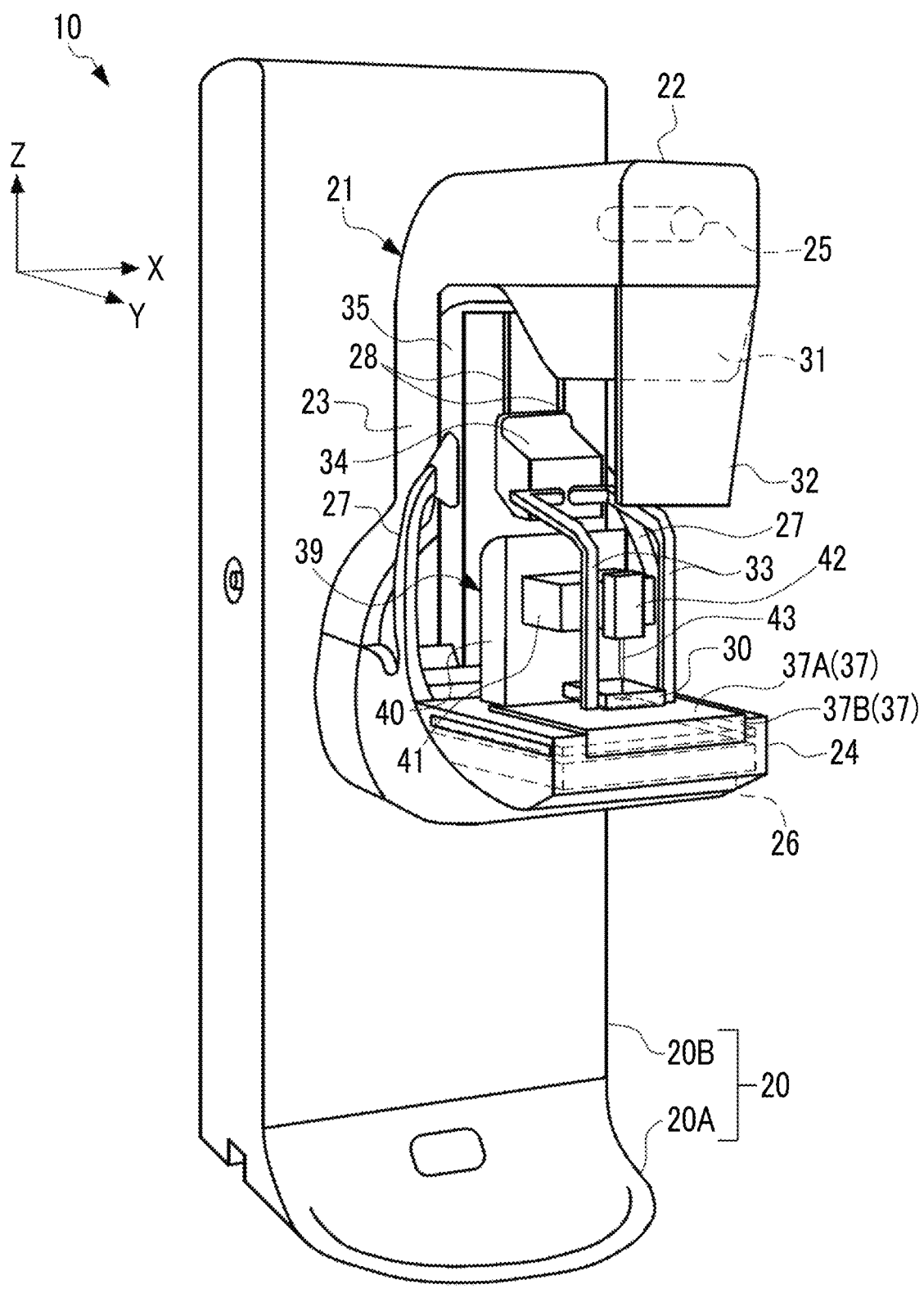
FIG. 1 is an exterior perspective view showing an example of a configuration of a mammography apparatus.
Figure 2:
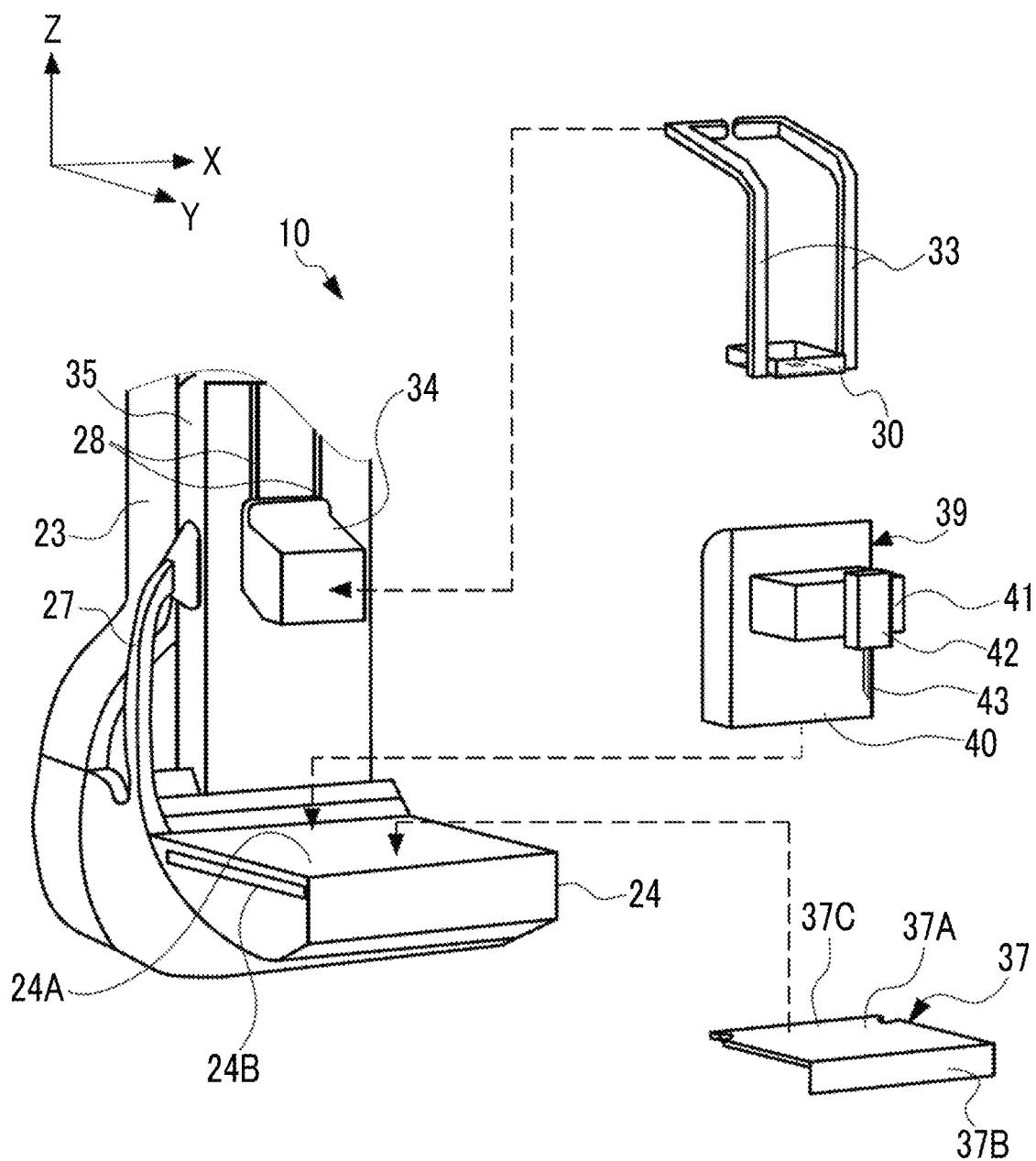
FIG. 2 is an exterior perspective view showing an example of a state in which a protective cover and a biopsy unit are attached to and detached from the mammography apparatus.

As shown in FIG. 1 and FIG. 2, the mammography apparatus 10 according to a first embodiment is a radiography apparatus that emits radiation to a breast M of a subject A as a subject and captures a radiation image of the breast M. The radiation is, for example, X-rays, but γ-rays may also be used. The subject A is located on a front side of the mammography apparatus 10. The mammography apparatus 10 is an example of a "mammography apparatus" according to the technology of the present disclosure.

The mammography apparatus 10 is connected to a console (not shown). The console has a function of acquiring the radiation image captured by the mammography apparatus 10 and displaying the acquired radiation image, in addition to a setting function of setting the mammography apparatus 10 according to an imaging order. The console is communicably connected to an image database server (not shown) via a network (not shown), such as a local area network (LAN).

The mammography apparatus 10 is provided with a stand 20 and an arm 21. The stand 20 is configured by using a seat 20A installed on a floor of a radiography room and a support column 20B that extends in the height direction from the seat 20A. The arm 21 has a substantially C-shape as viewed from the left side, and is connected to the support column 20B via a rotation axis. Since the arm 21 can be moved in the height direction with respect to the support column 20B, a height thereof can be adjusted according to a height of the subject A. In addition, the arm 21 can rotate about the rotation axis perpendicular to the support column 20B.

The arm 21 is configured by using a radiation source housing part 22, a body part 23, and an imaging table 24. A radiation source 25 is housed in the radiation source housing part 22. The radiation source housing part 22 has, for example, a housing structure having a longitudinal direction in the front-rear direction. The breast M of the subject A is placed on the imaging table 24. A radiation detector 26 is housed in the imaging table 24. The body part 23 integrally connects the radiation source housing part 22 and the imaging table 24. The body part 23 holds the radiation source housing part 22 and the imaging table 24 at positions that face each other. Handrails 27 for the subject A to grip are provided on both sides of the body part 23.

The breast M of the subject A is placed on the imaging table 24. The imaging table 24 comprises an imaging surface 24A on which the radiation transmitted through the breast M is incident. A radiation detector 26 is housed in the imaging table 24. The imaging table 24 is an example of an "imaging table" according to the technology of the present disclosure.

The radiation source 25 irradiates the breast M placed on the imaging table 24 with the radiation. The radiation emitted from the radiation source 25 is transmitted through a compression plate 30, and then incident on the breast M. The radiation detector 26 detects the radiation transmitted through the breast M, and outputs the radiation image. The radiation detector 26 is referred to as a flat panel detector (FPD). The radiation detector 26 may be an indirect conversion type that includes a scintillator converting the radiation into visible light and converts the visible light emitted from the scintillator into an electric signal, or may be a direct conversion type that directly converts the radiation into an electric signal. The radiation detector 26 is an example of a "detector" according to the technology of the present disclosure.

An irradiation field limiter 31 is provided between the radiation source 25 and the imaging table 24. The irradiation field limiter 31 is also referred to as a collimator, and defines an irradiation field of the radiation to the imaging table 24.

A face guard 32 is attached to the radiation source housing part 22. The face guard 32 is made or coated with a material that does not transmit the radiation, and protects a face of the subject A from the radiation.

The compression plate 30 that interposes and compresses the breast M with the imaging table 24 is provided between the imaging table 24 and the irradiation field limiter 31. The compression plate 30 is made of a material that transmits the radiation. The compression plate 30 is disposed at a position that faces the imaging table 24. In the present embodiment, the compression plate 30 is formed in a box shape with an open upper surface side.

A moving mechanism 35 supports the compression plate 30 to be movable between the radiation source 25 and the imaging table 24. In addition, the movable part 34 is disposed between the compression plate 30 and the moving mechanism 35. The movable part 34 is held by a rail 28 provided on the moving mechanism 35 to be movable slidingly. The rail 28 stretches in the up-down direction.

The moving mechanism 35 includes, for example, a motor (not shown), a motor driver (not shown), and a feed screw mechanism (not shown). The motor rotates according to an electric drive signal output by the motor driver, and moves the compression plate 30 via the feed screw mechanism.

The compression plate 30 is attached to the movable part 34 via a pair of support arms 33. The movable part 34 is moved in the up-down direction together with the compression plate 30 by the moving mechanism 35. The up-down direction refers to, functionally, a direction in which the compression plate 30 is directed toward the imaging table 24 (that is, the down direction) and a direction in which the compression plate 30 is separated from the imaging table 24 (that is, the up direction). As described above, the compression plate 30 is configured to be movable in an aspect in which an interval with the imaging table 24 is changed.

A biopsy unit 39 is attached to the mammography apparatus 10. The biopsy unit 39 is a unit that samples tissue in the breast M to perform a biological tissue sampling examination. The biopsy unit 39 comprises a body part 40, an adjustment part 41, a needle holding part 42, and a puncture needle 43. The adjustment part 41 can be moved with respect to the body part 40, and as a result, an insertion position, an insertion angle, and an insertion amount of the puncture needle 43 with respect to the breast M are adjusted. The needle holding part 42 holds the puncture needle 43. The puncture needle 43 has, for example, a double structure of an outer needle and an inner needle. As an example, a procedure for sampling the tissue with the puncture needle 43 is as follows. In a state in which the puncture needle 43 is inserted into the breast M and a tip end portion of the puncture needle 43 reaches a position of the tissue that is a sampling target, the inner needle is protruded from the outer needle to sample the tissue into a tissue sampling region formed on the inner needle. After sampling the tissue in the inner needle, the inner needle is housed in the outer needle, and the puncture needle 43 is pulled out from the breast M. As a result, the tissue that is the sampling target in the breast M is sampled. In addition, the compression plate 30 is provided with an opening on a bottom surface, and the puncture needle 43 is inserted into the breast M via the opening.

In a case in which a biopsy is performed by using the biopsy unit 39, a protective cover 37 is placed on the imaging table 24. The protective cover 37 protects the imaging surface 24A from the puncture needle 43. That is, the contact of the puncture needle 43 with the imaging surface 24A is suppressed by the protective cover 37. The protective cover 37 comprises a flat plate-shaped protective member 37A and a front wall 37B bent from a front end of the protective member 37A. The breast M is placed on the protective member 37A. The protective member 37A is made of a material that can transmit the radiation (for example, an acrylic resin). A size of the protective member 37A is a size in a range that can support the breast M, and a plate thickness of the protective member 37A has a strength that can support the breast M.

As shown in FIG. 2, the biopsy unit 39 and the protective cover 37 are attached to the mammography apparatus 10 in a case in which the biopsy is performed. Stated another way, the biopsy unit 39 and the protective cover 37 are attachable to and detachable from the mammography apparatus 10. The protective cover 37 is attached to the imaging table 24 of the mammography apparatus 10 by utilizing, for example, magnetic attraction using a magnet. Specifically, the magnet is attached to the protective cover 37, and the magnet is magnetically attracted to a magnetizing plate provided on the imaging table 24 to attach the protective cover 37 to the imaging table 24. It should be noted that this is merely an example, and for example, the protective cover 37 may be attached to the imaging table 24 via a pressure-sensitive adhesive sheet, or the protective cover 37 may be attached to the imaging table 24 by fitting a part of the protective cover 37 into a recess provided in the imaging table 24.

The biopsy unit 39 is placed on the imaging table 24 after the protective cover 37 is attached to the imaging table 24. Specifically, the body part 40 of the biopsy unit 39 is placed above a rear end portion 37C of the protective cover 37. It should be noted that the biopsy unit 39 may be controlled to operate only in a case in which the protective cover 37 is attached to the imaging table 24.

Also, the compression plate 30 is a compression plate for the biopsy unit 39, and is attached to the mammography apparatus 10 by replacing the compression plate 30 with a compression plate for mammography (not shown) in a case in which the biopsy is not performed.

Figure 3:
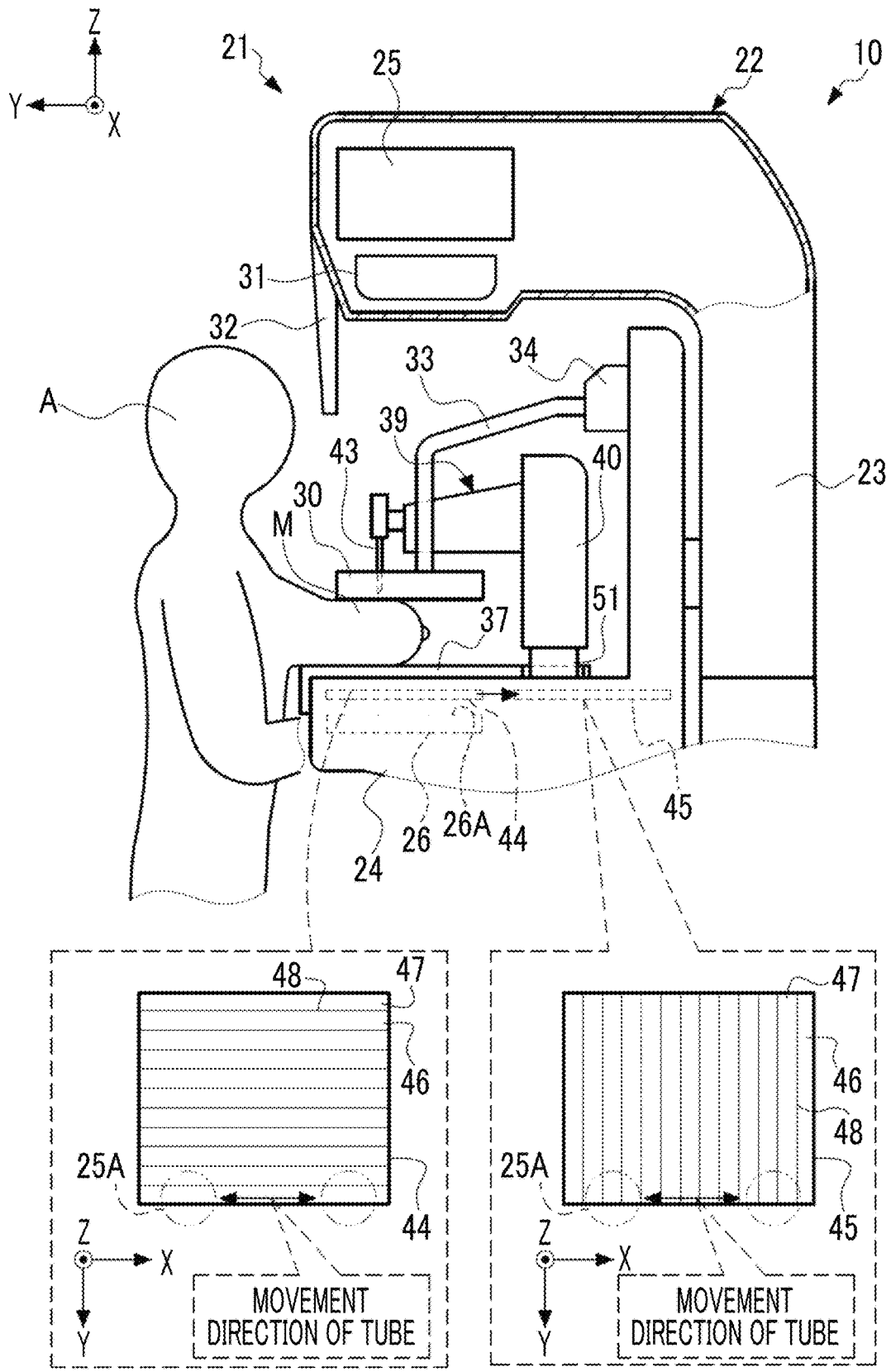
FIG. 3 is an exterior side view showing an example of the configuration of the mammography apparatus.

As shown in FIG. 3, for example, in a case in which the biopsy is performed, the puncture needle 43 is inserted into the breast M in a state in which the breast M is compressed by the compression plate 30. In such a case, it is required to accurately specify the position of the tissue (for example, a lesion tissue) that is the sampling target of the breast M. For this reason, as will be described below, in a case in which the biopsy is performed, in some cases, stereo imaging of emitting the radiation R toward the breast from two left and right directions having different irradiation angles with respect to the imaging table 24 is performed to three-dimensionally specify the position of the tissue that is the sampling target in the breast M.

Here, there is a case in which a scattered ray removal grid is built in the imaging table 24, as in a built-in grid 45. The scattered ray removal grid, as is well known, removes scattered rays generated by the radiation R transmitting through the breast M. The built-in grid 45 is disposed inside the imaging table 24 on a side of the radiation source 25 with respect to the radiation detector 26. The built-in grid 45 is a flat plate-shaped member, and comprises a transmission part 47 that transmits the radiation R and an absorption part 46 that absorbs the radiation R. The absorption parts 46 and the transmission parts 47 are alternately arranged, and a boundary line 48 between the absorption part 46 and the transmission part 47 is disposed inside the imaging table 24 in a state of extending in the front-rear direction (that is, a direction connecting a chest wall side and an anti-chest wall side of the subject A on the imaging surface 24A). Stated another way, the absorption parts 46 and the transmission parts 47 are alternately arranged in the left-right direction.

Examples of a material of the absorption part 46 include a thin film of lead. In addition, examples of a material of the transmission part 47 include aluminum, paper, and carbon fiber.

In a case in which the stereo imaging is performed, in the mammography apparatus 10, the imaging is performed in a state in which the built-in grid 45 is moved to an anti-chest wall side (that is, a side of the body part 23) inside the imaging table 24. In the built-in grid 45, the boundary line 48 between the absorption part 46 and the transmission part 47 extends in a direction orthogonal to a movement direction of a tube 25A. Therefore, in a case in which the imaging is performed by moving the tube 25A by using the built-in grid 45, a central axis of a flux of the radiation R and the boundary line 48 are orthogonal to each other, and thus vignetting of the radiation is increased.

Therefore, in the stereo imaging, an insertion grid 44, which is a scattered ray removal grid inserted into the imaging table 24 from the outside, is used instead of the built-in grid 45. The insertion grid 44 means a scattered ray removal grid inserted into the imaging table 24 from the outside, and is used here for distinction from the built-in grid 45 built in the imaging table 24. The insertion grid 44 comprises the absorption part 46 and the transmission part 47, similarly to the built-in grid 45. In the insertion grid 44, the absorption parts 46 and the transmission parts 47 are alternately arranged, and the boundary line 48 between the absorption parts 46 and the transmission parts 47 extends in the left-right direction. Stated another way, the absorption parts 46 and the transmission parts 47 are alternately arranged in the front-rear direction. As a result, in the insertion grid 44, the central axis of the flux of the radiation R and an extending direction of the boundary line 48 substantially match, so that the occurrence of vignetting of the radiation is suppressed in the stereo imaging. The absorption part 46 is an example of an "absorption part" according to the technology of the present disclosure, and the transmission part 47 is an example of a "transmission part" according to the technology of the present disclosure. The boundary line 48 is an example of a "boundary line" according to the technology of the present disclosure. The insertion grid 44 is an example of a "scattered ray removal grid" and an "external grid" according to the technology of the present disclosure. The built-in grid 45 is an example of a "built-in grid" according to the technology of the present disclosure.

The built-in grid 45 can be moved in the imaging table 24 between a facing position facing a detection surface 26A of the radiation detector 26 and a retreat position retreating from the facing position. In the example shown in FIG. 3, the built-in grid 45 is moved to the retreat position that is a position behind the radiation detector 26 inside the imaging table 24. The insertion grid 44 is disposed at the facing position. The detection surface 26A is an example of a "detection surface" according to the technology of the present disclosure.

Figure 4:
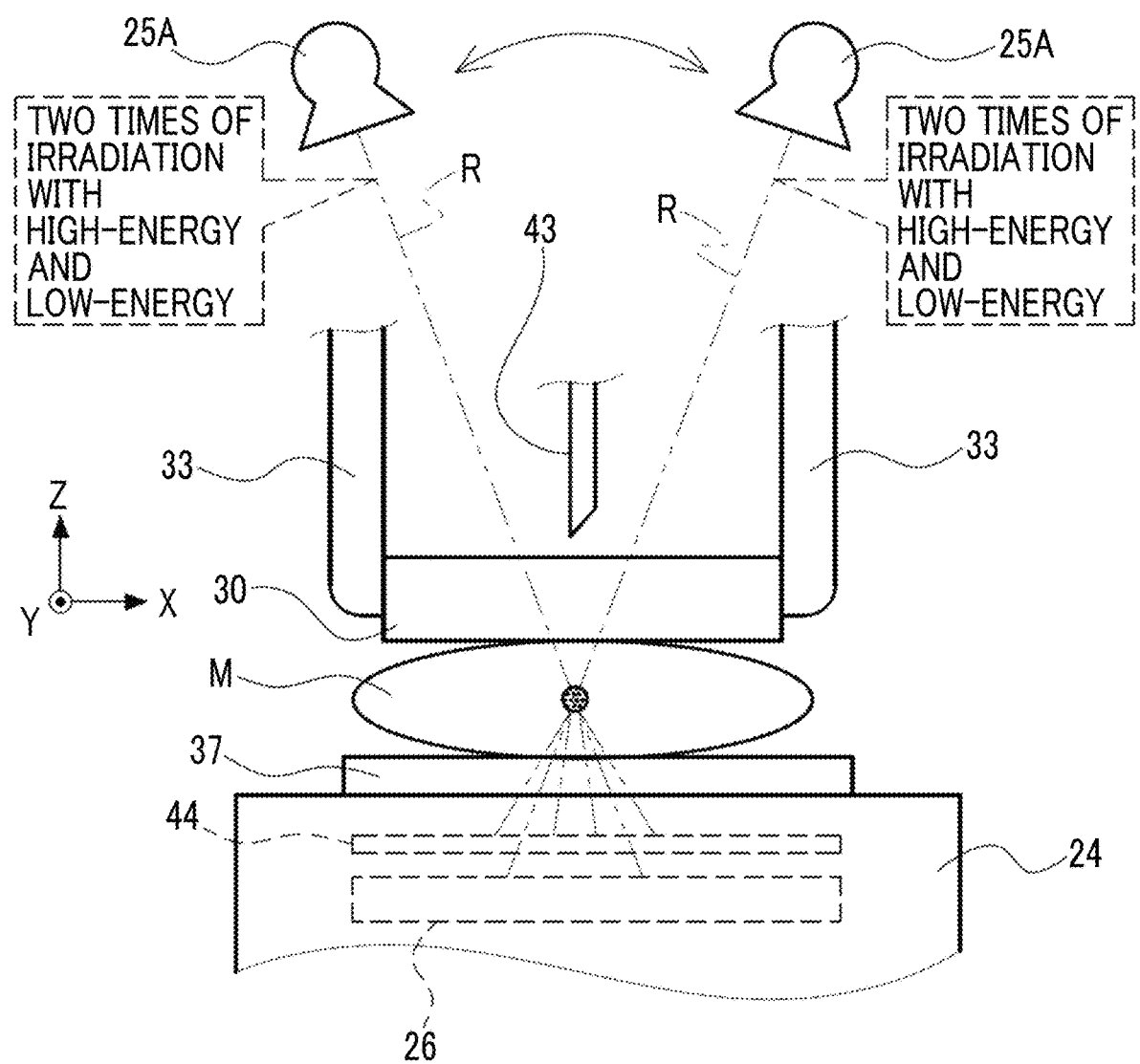
FIG. 4 is an exterior front view showing an example of the configuration of the mammography apparatus.

As shown in FIG. 4, the mammography apparatus 10 has a function of performing contrast imaging. As a contrast agent used for the contrast imaging, a contrast agent using iodine having a k-absorption edge of 33 keV (hereinafter, simply referred to as a "contrast agent") is generally used. The mammography apparatus 10 uses the breast M to which the contrast agent is administered as the subject, captures a low-energy image by using the radiation detector 26 by emitting the radiation R having a first energy lower than the k-absorption edge of the contrast agent, and captures a high-energy image by using the radiation detector 26 by emitting the radiation R having a second energy higher than the k-absorption edge of the contrast agent. Specific first energy and second energy are determined from specifications of the mammography apparatus 10, a desired image quality of the radiation image, and exposure of the subject or the like in addition to the k-absorption edge of the contrast agent, and are generally preferably 22 keV to 49 keV.

The contrast agent and the tissue, such as a mammary gland, have different absorption characteristics of the radiation R. Therefore, in the high-energy image captured as described above, a body tissue, such as the mammary gland or fat, is shown, and the contrast agent is clearly reflected. In addition, in the low-energy image, almost no contrast agent is shown, and the body tissue, such as the mammary gland, is clearly reflected. Therefore, a difference image showing a difference between the low-energy image and the high-energy image can be made to be an image in which a mammary gland structure is removed and the contrast agent is clearly shown. This imaging is referred to as contrast energy subtraction imaging.

Further, as described above, in a case of the biopsy, there is a case in which the stereo imaging is performed to three-dimensionally grasp the position of the tissue that is a biopsy target in the breast M. In the stereo imaging, an irradiation position of the radiation R is changed in the left-right direction, so that the irradiation angle of the radiation R is changed and the imaging is performed a plurality of times. The imaging with the radiation R having different energies (that is, the contrast energy subtraction imaging) is performed at each irradiation angle in the left-right direction in the stereo imaging. As a result, the tissue that is the biopsy target is clear in the image, and it is easier to grasp the three-dimensional position.

The stereo imaging is performed in a state in which the breast M is compressed between the compression plate 30 and the protective cover 37. The insertion grid 44 is provided between the imaging surface 24A of the imaging table 24 and the radiation detector 26. The radiation R in which the scattered rays are removed by the insertion grid 44 is incident on the radiation detector 26. The high-energy image and the low-energy image can be obtained at each irradiation angle in the left-right direction. Then, after grasping the three-dimensional position of the tissue that is the biopsy target in the breast M by the stereo imaging, the puncture needle 43 is inserted into the breast M to sample the tissue that is the biopsy target.

Figure 5:
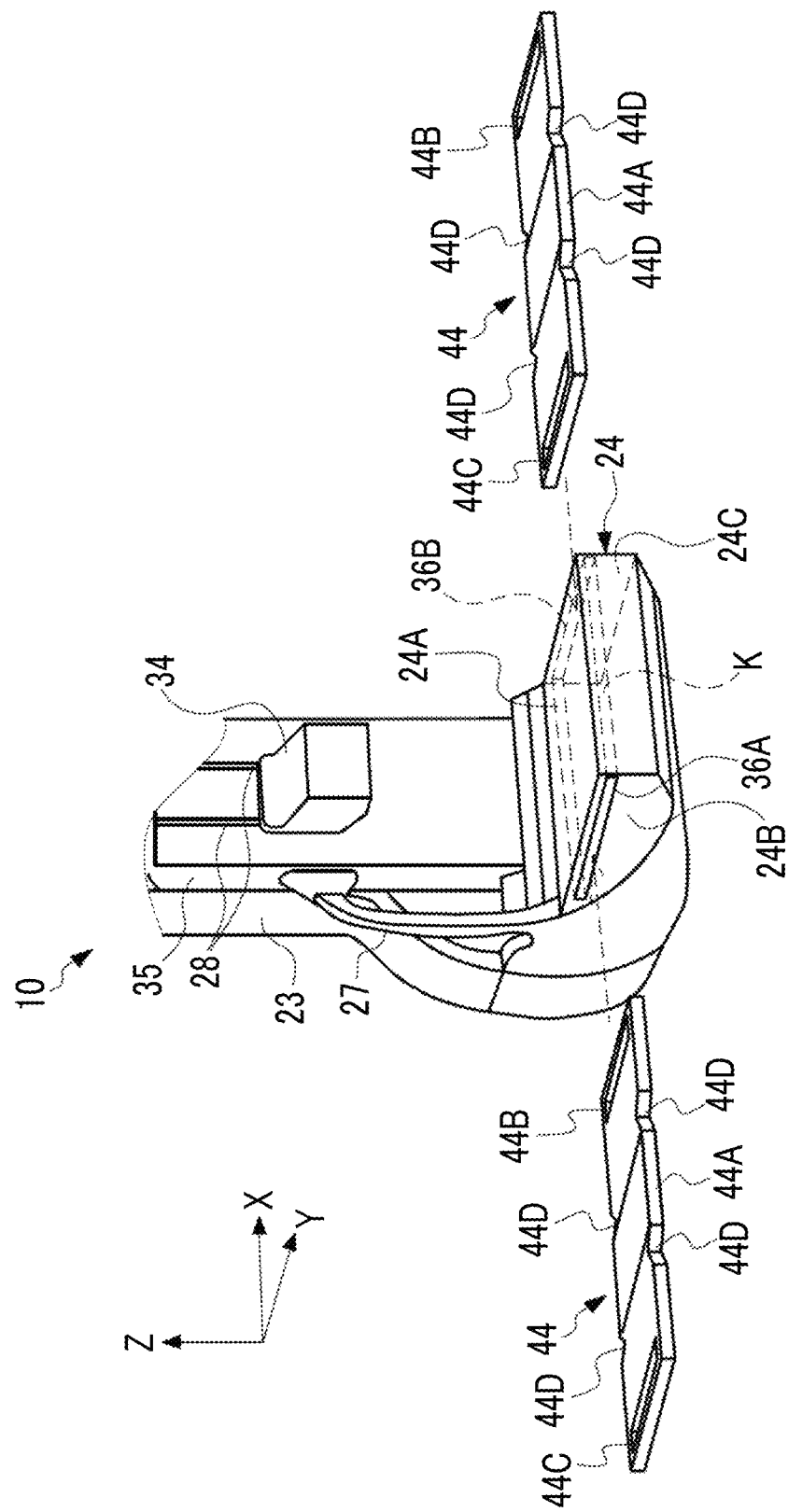
FIG. 5 is an exterior perspective view showing an example of a state in which an insertion grid is inserted into an imaging table.

As shown in FIG. 5, the insertion grid 44 is inserted from any one of the left-right direction of the imaging table 24. An opening 36A is formed in a left side surface 24B of the imaging table 24. Further, an opening 36B is formed in a right side surface 24C of the imaging table 24. The opening 36A and the opening 36B communicate with a space K formed inside the imaging table 24, and the insertion grid 44 is inserted into the space K via the opening 36A or the opening 36B. The space K is formed by the built-in grid 45 moving to the rear side inside the imaging table 24. It should be noted that the opening 36A and the opening 36B do not have to be always open, and may have, for example, an aspect in which a cover (not shown) is opened and closed as necessary. The opening 36A and the opening 36B are examples of an "opening" according to the technology of the present disclosure. The left side surface 24B is an example of a "left side surface" according to the technology of the present disclosure, and the right side surface 24C is an example of a "right side surface" according to the technology of the present disclosure.

Here, on the front side of the mammography apparatus 10, the subject A is located. In a case in which the imaging is performed on the right breast M of the subject A, the subject A is located to face the left side of the mammography apparatus 10 from a position confronting the mammography apparatus 10. In such a case, a user inserts the insertion grid 44 from the left side of the mammography apparatus 10. On the other hand, in a case in which the imaging is performed on the left breast M of the subject A, the subject A is located to face the right side of the mammography apparatus 10 from the confronting position. In such a case, the user inserts the insertion grid 44 from the right side of the mammography apparatus 10. In this way, since the insertion grid 44 can be inserted from both sides of the imaging table 24 in the left-right direction, the insertion direction of the insertion grid 44 can be changed according to a posture of the subject A.

The insertion grid 44 comprises a grid body 44A, grip parts 44B and 44C, and a recess part 44D. In the grid body 44A, the absorption part 46 and the transmission part 47 described above are formed. The grip parts 44B and 44C are parts gripped by the user in a case in which the insertion grid 44 is inserted into the imaging table 24. The grip parts 44B and 44C are examples of a "grip member" according to the technology of the present disclosure. In the example shown in FIG. 5, the grip parts 44B and 44C are attached to both end portions of the grid body 44A in the left-right direction in which the insertion grid 44 is inserted into the imaging table 24. The recess part 44D is a recess engaging with a protrusion as a fixing mechanism, which will be described below, and is provided between the grid body 44A and the grip parts 44B and 44C. In the example shown in FIG. 5, an example in which four recess parts 44D are provided is shown.

Figure 6:
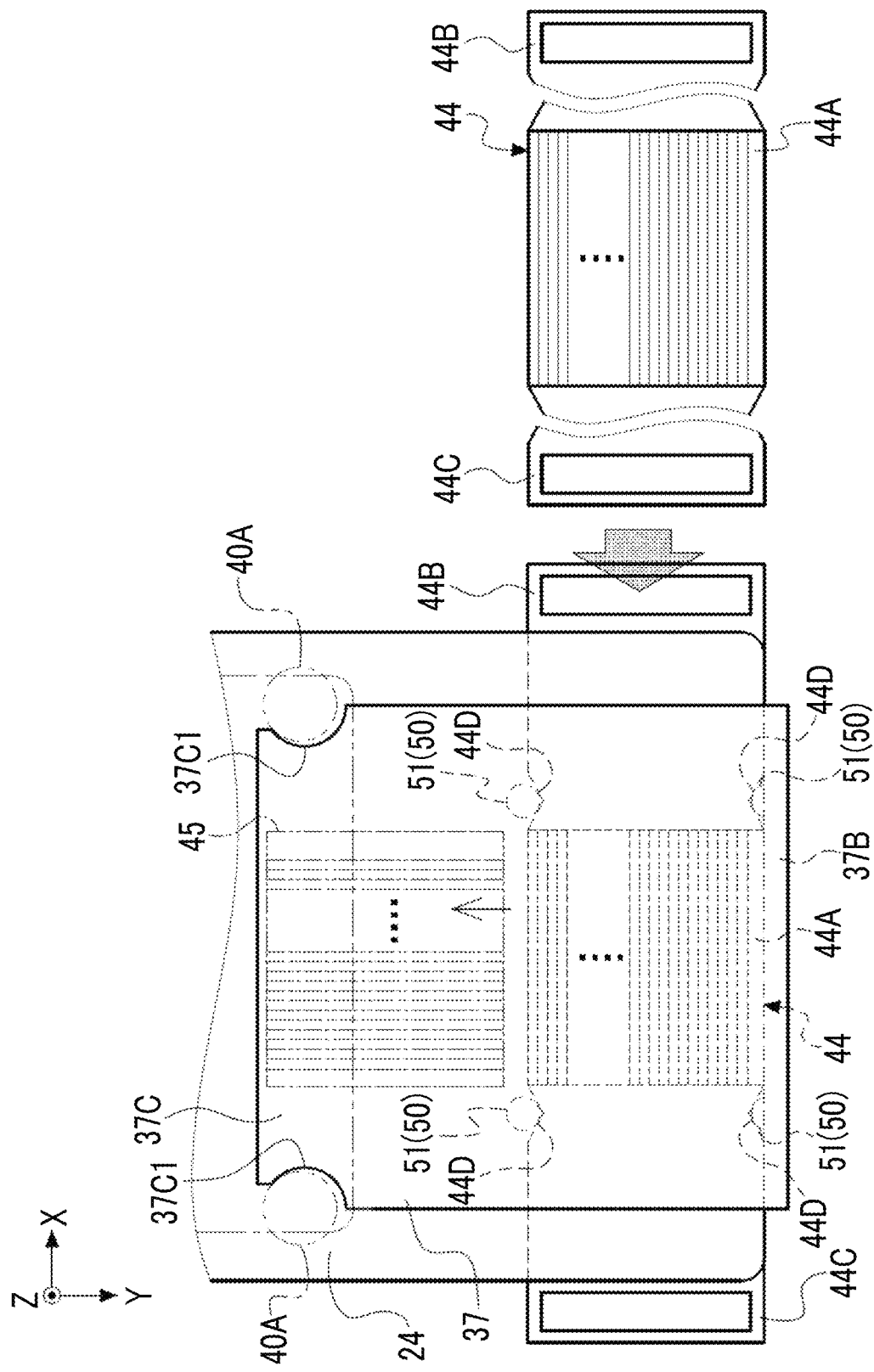
FIG. 6 is an exterior plan view showing an example of a state in which the insertion grid is inserted into the imaging table.

As shown in FIG. 6, in a case in which the insertion grid 44 is inserted into the imaging table 24, the built-in grid 45 is first moved to the rear side in the imaging table 24. As a result, the space K is formed inside the imaging table 24. The insertion grid 44 is inserted into the imaging table 24 from the left-right direction. In the example shown in FIG. 6, an example in which the insertion grid 44 is inserted from the right side of the imaging table 24 is shown. A fixing mechanism 50 that fixes the insertion grid 44 at a predetermined position (for example, a position at which the insertion grid 44 faces the detection surface of the radiation detector 26) inside the imaging table 24 is provided inside the imaging table 24. The fixing mechanism 50 is an example of a "first fixing mechanism" according to the technology of the present disclosure.

The fixing mechanism 50 comprises four protrusions 51. The four protrusions 51 are provided at positions corresponding to the recess parts 44D of the insertion grid 44, and engage with the recess parts 44D to fix the insertion grid 44 to the inside of the imaging table 24. As a result, the insertion grid 44 is positioned inside the imaging table 24 at the position facing the detection surface 26A (see FIG. 3) of the radiation detector 26. The protrusion 51 is an example of a "protrusion" according to the technology of the present disclosure, and the recess part 44D is an example of a "recess part" according to the technology of the present disclosure.

It should be noted that, although the example in which the four protrusions 51 and the corresponding four recess parts 44D engage with each other is described here, this is merely an example. The number of the recess parts 44D and the number of the protrusions 51 can be appropriately set according to the positioning accuracy in a case in which the insertion grid 44 is fixed, the force required for the user to perform the insertion and drawing-out work of the insertion grid 44, and the like. In addition, the disposition and the shape of the recess part 44D and the protrusion 51 can also be appropriately set according to the positioning accuracy in a case in which the insertion grid 44 is fixed, the force required for the user to perform the insertion and drawing-out work of the insertion grid 44, and the like.

In the protective member 37A of the protective cover 37, an arc-like notch 37C1 is provided in the rear end portion 37C. Further, a pair of bases 40A are provided on the body part 40 of the biopsy unit 39. The base 40A has a columnar shape, and the notch 37C1 has a shape corresponding to an outer periphery of the base 40A. After the protective cover 37 is placed on the imaging table 24, the biopsy unit 39 is placed on the imaging table 24 from above. In such a case, the base 40A is placed at a position corresponding to the notch 37C1. As a result, even in a case in which the protective cover 37 is moved in the front-rear direction or the left-right direction, the notch 37C1 comes into contact with the base 40A, so that a significant displacement of the position of the protective cover 37 is suppressed. It should be noted that a gap is provided between the outer periphery of the base 40A and an inner periphery of the notch 37C1, and the movement of the protective cover 37 is allowed to some extent. As a result, the movement of the biopsy unit 39 with the movement of the protective cover 37 is suppressed, so that the displacement of the position of the puncture needle 43 provided in the biopsy unit 39 is suppressed.

Figure 7:
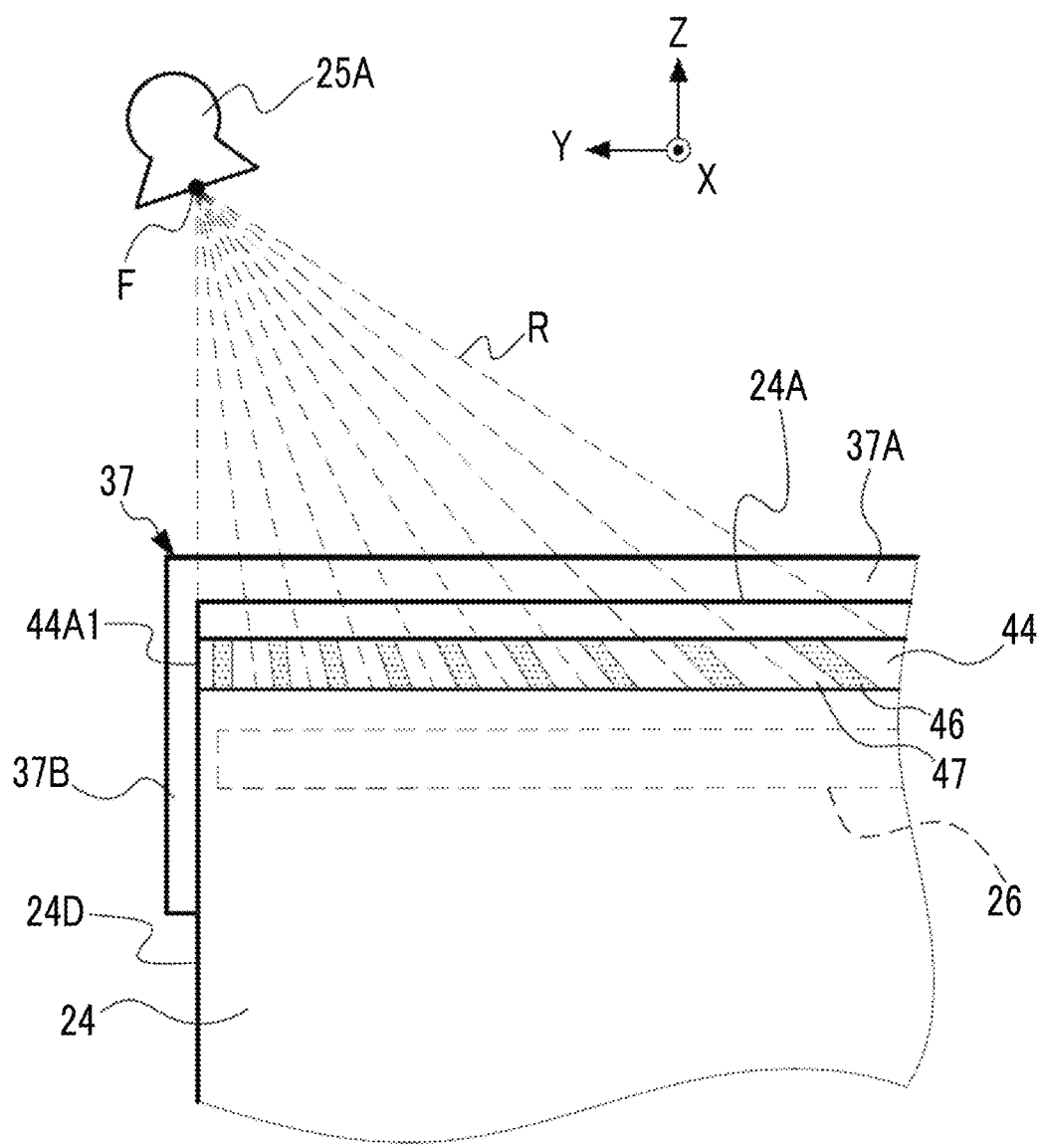
FIG. 7 is an exterior side view showing an example of a state in which radiation is emitted in the mammography apparatus.

As shown in FIG. 7, at the facing position, the insertion grid 44 is located at a position closest to a chest wall side (that is, the front side) on the imaging table 24. For example, the insertion grid 44 is disposed at a position at which a front end surface 44A1 of the insertion grid 44 and a front end surface 24D of the imaging table 24 match. A focal position of the tube 25A is disposed above the front end surface 24D of the imaging table 24. As a result, the image can be captured up to the chest wall side with respect to the breast M placed on the imaging table 24. Since the insertion grid 44 is located closest to the chest wall side on the imaging table 24, the scattered rays can be removed up to the chest wall side of the breast M that is an imaging target.

In addition, the insertion grid 44 is a so-called focused grid. That is, in the insertion grid 44, a plurality of boundary surfaces of the absorption parts 46 and the transmission parts 47 are not parallel to each other, and a surface obtained by extending each of the plurality of boundary surfaces is inclined in an aspect in which the surface passes through a focal position F of the tube 25A and is focused on one straight line parallel to the boundary surface. In the present example, since the focal position F of the tube 25A is disposed on the side of the front end surface 44A1 of the insertion grid 44, inclination angles of the plurality of boundary surfaces are gradually increased from the front end surface 44A1 toward the rear side. By setting the insertion grid 44 as the focused grid, vignetting of the radiation R is further suppressed as compared with a parallel grid in which the plurality of boundary surfaces are parallel to each other.

In FIG. 8, imaging modes and the grids used in the mammography apparatus 10 according to the present embodiment are summarized. As shown in FIG. 8, the built-in grid 45 is used in the imaging (that is, normal imaging) in a case in which the radiation source 25 is located at a position that faces the imaging table 24 in the vertical direction (that is, normal imaging). The built-in grid 45 is, as described above, built in the imaging table 24. In the built-in grid 45, the boundary line 48 between the absorption part 46 and the transmission part 47 extends in the front-rear direction.

On the other hand, the insertion grid 44 inserted into the imaging table 24 is used in a case of the stereo imaging. The insertion grid 44 is inserted into the imaging table 24 and thus is provided between the imaging surface 24A and the radiation detector 26. In the insertion grid 44, the boundary line 48 between the absorption part 46 and the transmission part 47 extends in the left-right direction (in the present example, the movement direction of the tube 25A). As described above, it is possible to select the scattered ray removal grid suitable for the imaging mode.

As described so far, in the mammography apparatus 10 according to the first embodiment, the openings 36A and 36B are provided in the side surfaces of the imaging table 24. The insertion grid 44 can be inserted from at least any one of the imaging table 24 in the left-right direction, and thus the insertion grid 44 can be inserted into the imaging table 24 even in a state in which the subject A is located on the front side of the imaging table 24 can be inserted. As a result, it is possible to facilitate the work of changing the scattered ray removal grid as compared with a case in which the opening for inserting the grid is not provided.

In addition, for example, since the insertion grid 44 can be disposed inside the imaging table 24, the insertion grid 44 can be disposed closer to the detection surface 26A of the radiation detector 26 than in a case in which the grid is disposed outside the imaging table 24, and thus the effect of removing the scattered rays is improved.

In the mammography apparatus 10 according to the first embodiment, the opening 36A is provided in the left side surface 24B of the imaging table 24, and the opening 36B is provided in the right side surface 24C. As a result, the insertion grid 44 can be inserted from any direction of the left-right direction of the imaging table 24, and thus the insertion direction can be changed according to the direction of the body of the subject A. As a result, it is possible to facilitate the work of changing the scattered ray removal grid as compared with a case in which the opening for inserting the insertion grid 44 is provided only on one side of the imaging table 24.

Figure 9:
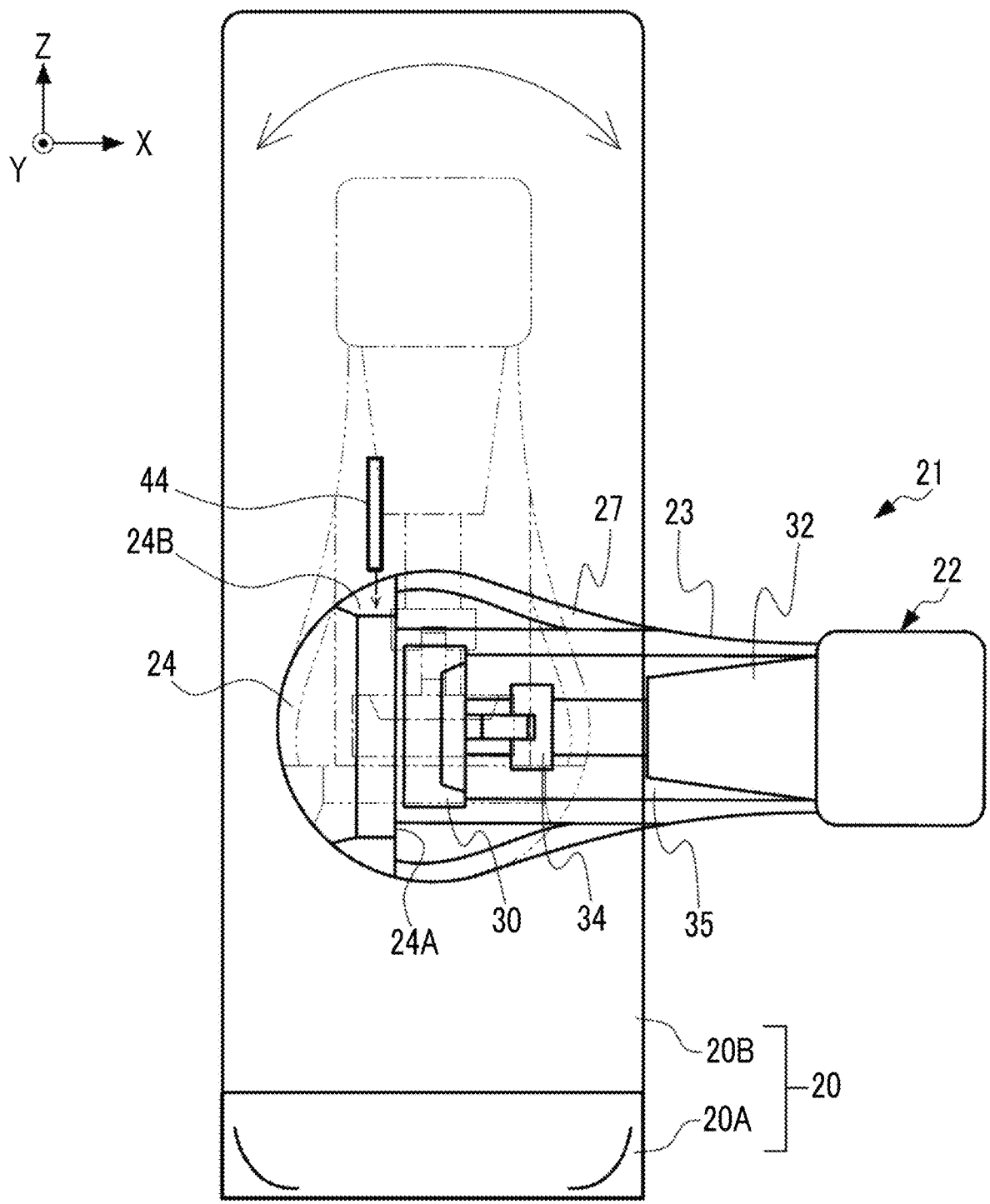
FIG. 9 is an exterior front view showing an example of a state in which the insertion grid is inserted into the imaging table in a state in which an arm is rotated in the mammography apparatus.

In addition, for example, as shown in FIG. 9, the imaging may be performed in a state in which the arm 21 is rotated with respect to the stand 20. In such a case, in a case in which an angle of the arm 21 with respect to the stand 20 is, for example, 90 degrees, one of the left side surface or the right side surface of the imaging table 24 is located on the upper side, and the other thereof is located on the lower side. In this state, in a case in which the insertion grid 44 is inserted into the imaging table 24, the insertion work is easier in a case in which the insertion is performed from the upper side than in a case in which the insertion is performed from the lower side. In the example shown in FIG. 9, the insertion grid 44 can be inserted from the left side surface 24B, which is the upper side among the left and right side surfaces. In the present configuration, the opening 36A is provided in the left side surface 24B of the imaging table 24, and the opening 36B is provided in the right side surface 24C. As a result, the insertion of the insertion grid 44 is easily performed even in a state in which the arm 21 is rotated with respect to the stand 20.

In addition, in the mammography apparatus 10 according to the first embodiment, the insertion grid 44 is the scattered ray removal grid suitable for the stereo imaging. That is, in a case in which the biopsy is performed, there is a case in which the stereo imaging is performed to three-dimensionally grasp the position of the tissue that is the biopsy target in the breast M. In the stereo imaging, an irradiation position of the radiation R is changed in the left-right direction, so that the irradiation angle of the radiation R is changed and the imaging is performed a plurality of times. With the present configuration, the insertion grid 44 can be disposed in the posture in which the extending direction in which the boundary line 48 of the absorption part 46 and the transmission part 47 of the insertion grid 44 is parallel to the left-right direction. For this reason, as compared with a case in which the insertion grid 44 is disposed in a posture in which the extending direction of the boundary line 48 is parallel to the front-rear direction, it is possible to suppress vignetting of the effective radiation R (radiation other than the scattered rays) that is obliquely incident from the radiation source 25 toward the imaging surface 24A. This is because, in a case in which the insertion grid 44 is disposed in the posture in which the extending direction of the boundary line 48 is parallel to the front-rear direction, the absorption part 46 that extends in parallel to the boundary line 48 and the central axis of the flux of the radiation R connecting the focal point of the tube 25A and the imaging surface 24A intersect with each other. That is, since the movement direction of the tube 25A and the extending direction of the absorption part 46 are orthogonal to each other, vignetting by the absorption part 46 occurs with respect to the radiation R emitted from the tube 25A.

Further, in a case of the biopsy, in order to acquire a breast image in which the biopsy target in which the new blood vessels are dense is emphasized, in some cases, the imaging in which the stereo imaging and the contrast energy subtraction imaging are combined is performed. The present configuration is particularly effective in such a case. This is because, in the contrast energy subtraction imaging, a difference between two images captured with the radiation having different energies is obtained, so that the contrast is likely to be decreased. In the present configuration, the incidence of the scattered rays is suppressed by using the insertion grid 44, so that the decrease in the contrast can be suppressed. It should be noted that, as a method of suppressing the decrease in the contrast, it is also conceivable to increase a gain of a signal output by the radiation detector 26 in image correction processing. However, since the noise is also increased in a case in which the gain is increased, the method using the insertion grid 44 is preferable.

Figure 10:
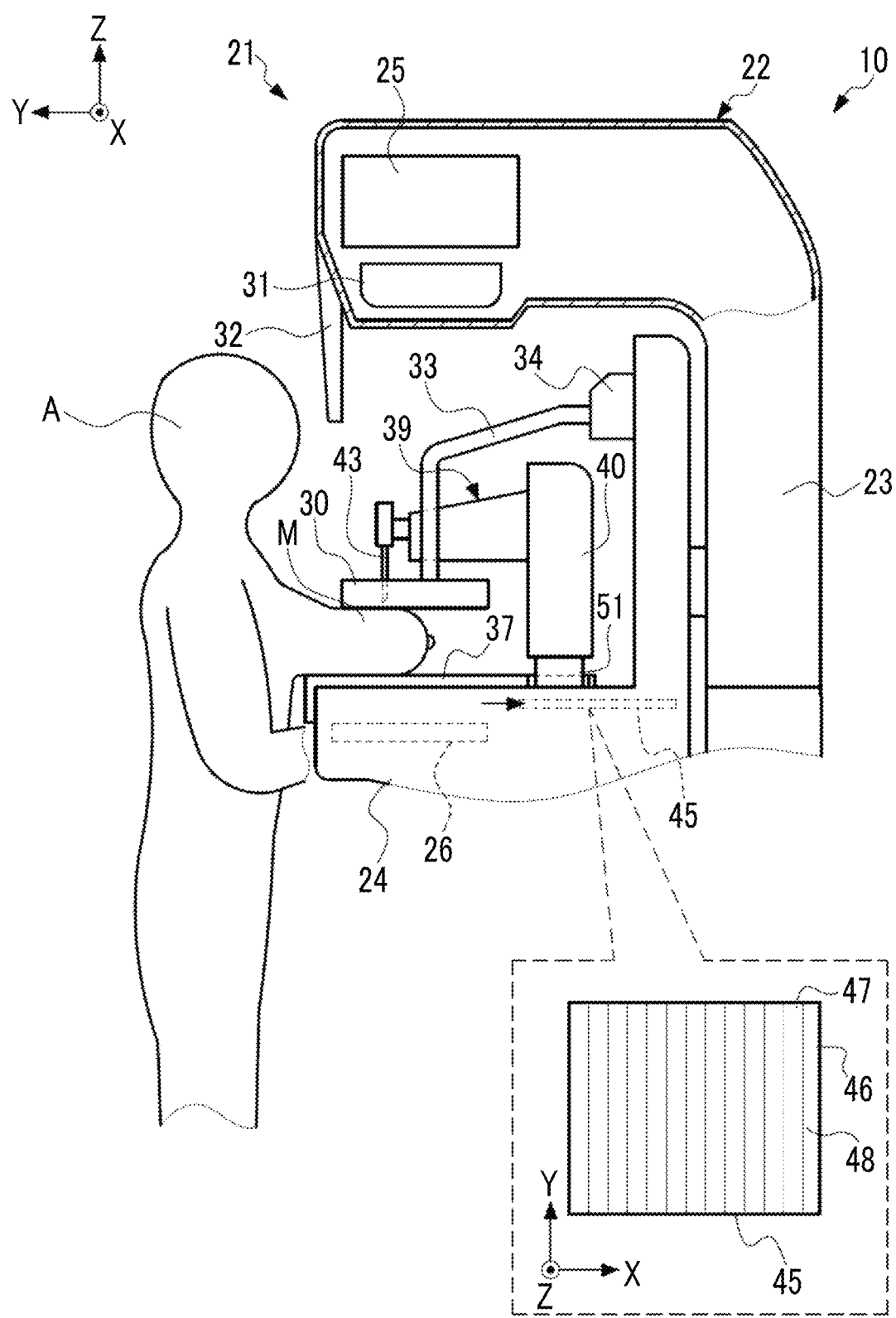
FIG. 10 is an exterior side view showing an example of a configuration of a mammography apparatus as a comparative example.
Figure 11:
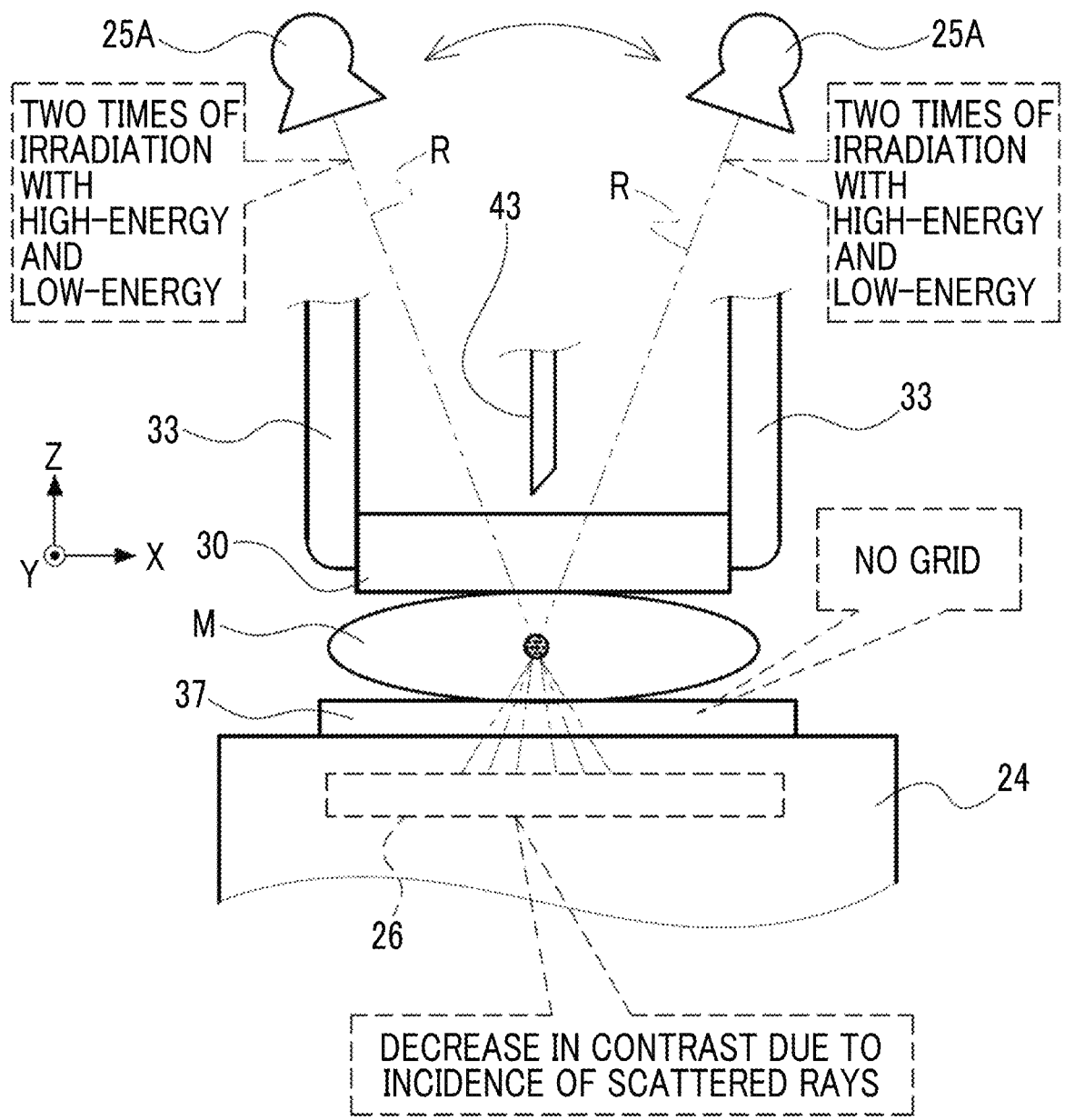
FIG. 11 is an exterior front view showing an example of the configuration of the mammography apparatus as the comparative example.

For example, as shown in FIG. 10 as a comparative example, a case will be considered in which imaging in which the stereo imaging and the contrast energy subtraction imaging are combined is performed in a state in which the built-in grid 45 is made to retreat without using the insertion grid 44. In such a case, since the built-in grid 45 retreats, vignetting of the radiation R due to the orthogonality between the movement direction of the tube 25A and the extending direction of the boundary line 48 does not occur. On the other hand, as shown in FIG. 11, since the insertion grid 44 is not used, the scattered rays caused by the radiation R transmitted through the breast M are directly incident on the radiation detector 26. As a result, the contrast in the breast image is decreased. As described above, in the contrast energy subtraction imaging, since the difference between the two images captured with the radiation having different energies is obtained, the contrast is likely to be decreased, and thus the contrast in the breast image is further decreased. As a result, it is difficult to grasp the position of the tissue that is the biopsy target in the breast M. In the present configuration, the incidence of the scattered rays is suppressed by using the insertion grid 44, so that the decrease in the contrast can be suppressed.

In addition, it is not assumed that the scattered ray removal grid is provided in a protective cover for a normal biopsy according to the comparative example. For this reason, even in a case in which there is a grid externally attached to the imaging table 24, the imaging table 24 is already covered with the protective cover, and thus the scattered ray removal grid cannot be disposed on the imaging table 24. In the present configuration, the insertion grid 44 can be inserted from the side surface of the imaging table 24, and thus it is possible to obtain the effect of removing the scattered rays by the insertion grid 44 while using the protective cover 37.

Further, in the mammography apparatus 10 according to the first embodiment, the fixing mechanism 50 is provided inside the imaging table 24. The fixing mechanism 50 fixes the insertion grid 44 at the position facing the detection surface 26A of the radiation detector 26. Accordingly, the positioning accuracy of the insertion grid 44 is improved as compared with a case in which the insertion grid 44 is not fixed.

Further, for example, since the fixing mechanism 50 is provided inside the imaging table 24, the designability of the mammography apparatus 10 is improved as compared with a case in which the fixing mechanism 50 is provided outside the imaging table 24.

In addition, in the mammography apparatus 10 according to the first embodiment, the fixing mechanism 50 includes the protrusion 51 that can engage with the recess part 44D provided in the insertion grid 44. In a case in which the insertion grid 44 is inserted into the imaging table 24, the protrusion 51 provided inside the imaging table 24 engages with the recess part 44D provided in the insertion grid 44. Accordingly, the insertion grid 44 is fixed inside the imaging table 24. In the present configuration, the protrusion 51 is provided on the mammography apparatus 10 side, and thus the opening areas of the openings 36A and 36B can be reduced as compared with a configuration in which the protrusion 51 is provided on the insertion grid 44 side. That is, in a case in which the insertion grid 44 passes through the openings 36A and 36B, the opening areas of the openings 36A and 36B can be reduced because there is no portion that protrudes from the insertion grid 44.

Further, in the mammography apparatus 10 according to the first embodiment, the insertion grid 44 is provided with the grip parts 44B and 44C. As a result, it is easier to perform the work of inserting the insertion grid 44 into the imaging table 24 or drawing out the insertion grid 44 from the inside of the imaging table 24 than in a case in which the grip parts 44B and 44C are not provided.

Further, in the mammography apparatus 10 according to the first embodiment, the insertion grid 44 is inserted into the imaging table 24 in a state in which the built-in grid 45 is moved to the retreat position. Since the insertion grid 44 is inserted into the space K generated by the retracting of the built-in grid 45, it is not necessary to separately form the space K inside the imaging table 24, and the size of the imaging table 24 can be reduced.

It should be noted that, in the first embodiment, the form example is described in which the fixing mechanism 50 has the protrusion 51, and the recess part 44D provided in the insertion grid 44 and the protrusion 51 engage with each other, so that the insertion grid 44 is fixed inside the imaging table 24, but the technology of the present disclosure is not limited to this. The fixing mechanism 50 need only be able to fix the insertion grid 44 to the inside of the imaging table 24. For example, an aspect may be adopted in which the fixing mechanism 50 may include a magnet and a magnetizing plate provided on the insertion grid 44 and the magnet are magnetically attracted to each other to fix the insertion grid 44.

Second Embodiment

In the first embodiment described above, the form example is described in which the protrusion 51 provided in the fixing mechanism 50 protrudes from an interior wall of the space K inside the imaging table 24, but the technology of the present disclosure is not limited to this. In the second embodiment, a protrusion 51A protrudes from a support member 54 that supports the radiation detector 26.

Figure 12:
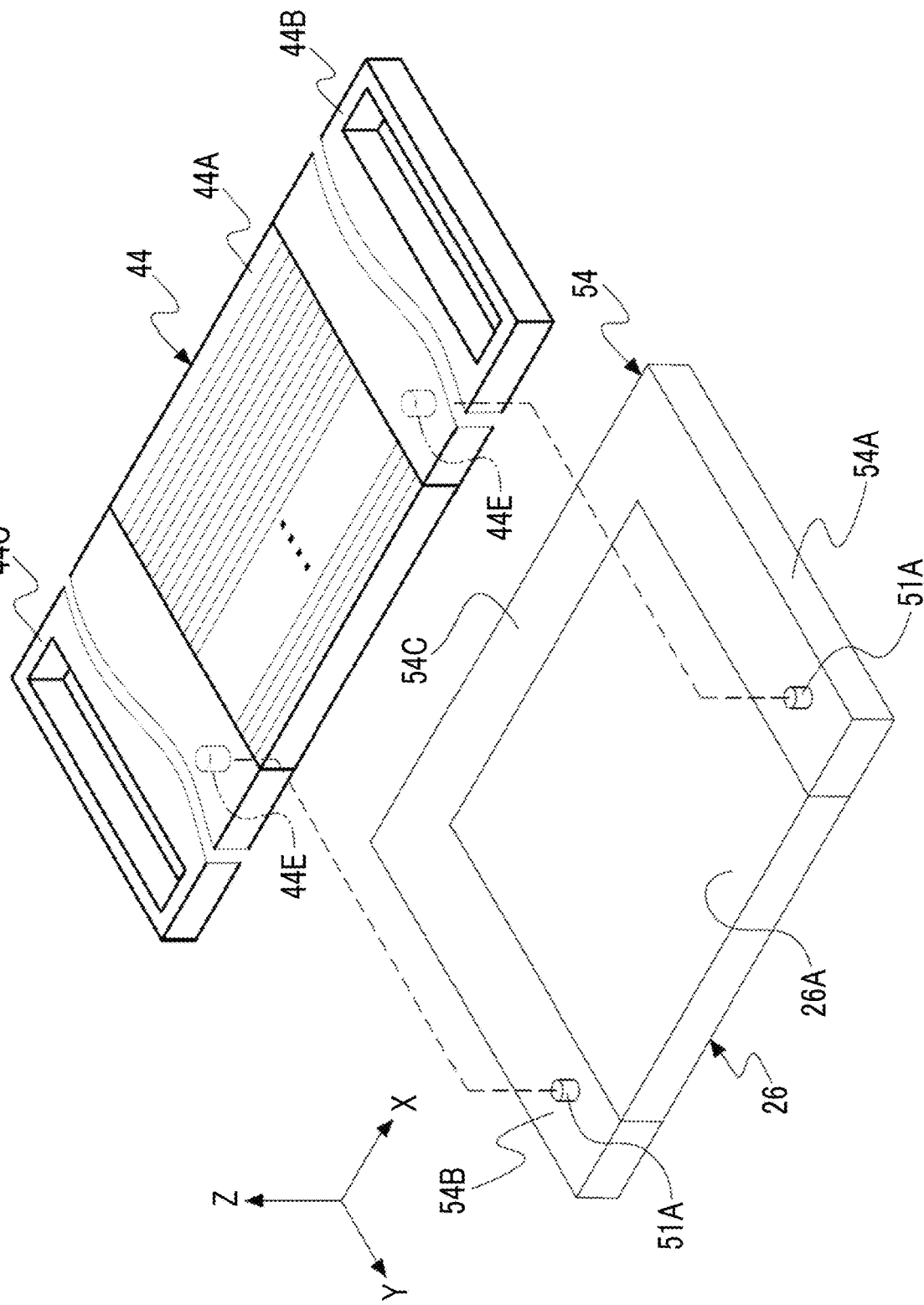
FIG. 12 is an exterior perspective view showing an example of a fixing mechanism.

As shown in FIG. 12, the radiation detector 26 is supported by the support member 54 inside the imaging table 24. The support member 54 is disposed on at least a part of a periphery of the detection surface 26A of the radiation detector 26. In the example shown in FIG. 12, the support member 54 is disposed on three sides of the periphery of the detection surface 26A of the radiation detector 26, that is, the right side, the left side, and the rear side. Stated another way, the support member 54 is not provided on the front side of the radiation detector 26 (that is, the chest wall side of the subject A). The support member 54 is an example of a "support member" according to the technology of the present disclosure.

Specifically, the support member 54 comprises a right side portion 54A, a left side portion 54B, and a rear side portion 54C. The right side portion 54A supports the right side of the periphery of the detection surface 26A, the left side portion 54B supports the left side of the periphery of the detection surface 26A, and the rear side portion 54C supports the rear side of the periphery of the detection surface 26A. Although not shown, the support member 54 is fixed to the interior wall of the space K inside the imaging table 24. In this way, the support member 54 supports the radiation detector 26. The support member 54 is made of, for example, metal.

Figure 13:
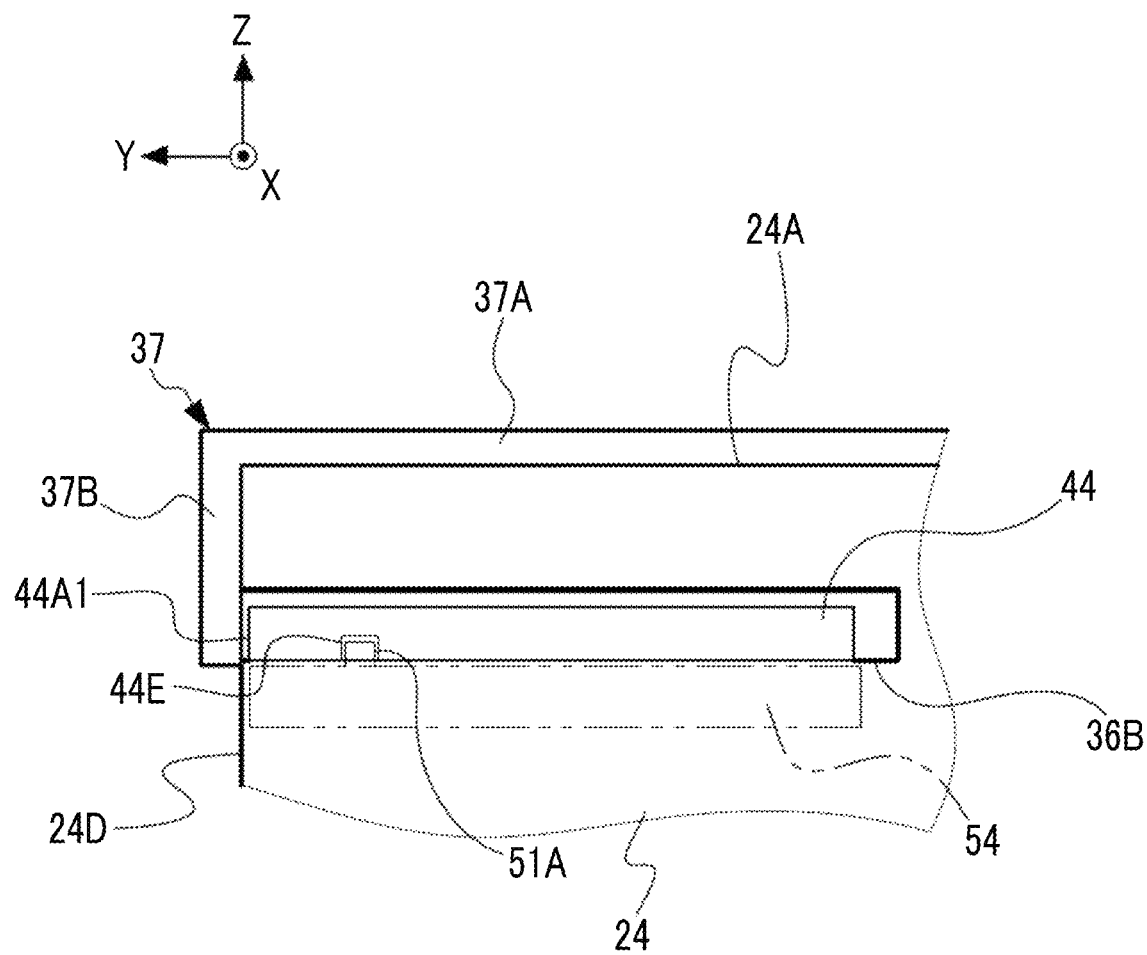
FIG. 13 is an exterior side view showing another example of the fixing mechanism.

The support member 54 is provided with the protrusion 51A. The protrusion 51A protrudes along a normal direction of the detection surface 26A (in the example shown in FIG. 12, the Z direction). Inside the imaging table 24, the protrusion 51A engages with a recess part 44E provided in the insertion grid 44. In the example shown in FIG. 12, the protrusion 51A is provided one by one on the right side portion 54A and the left side portion 54B, and forms a columnar shape. In the insertion grid 44, the recess part 44E is formed at a position corresponding to the protrusion 51A. Inside the imaging table 24, the insertion grid 44 disposed at the facing position is moved from above to below toward the radiation detector 26 and the support member 54. As a result, as shown in FIG. 13, the protrusion 51A engages with the recess part 44E. As a result, the insertion grid 44 is fixed inside the imaging table 24. The protrusion 51A is an example of a "protrusion" according to the technology of the present disclosure, and the recess part 44E is an example of a "recess part" according to the technology of the present disclosure.

As described so far, in the mammography apparatus 10 according to the second embodiment, the fixing mechanism 50 includes the protrusion 51A provided on the support member 54. The support member 54 is the member that is disposed on at least a part of the periphery of the radiation detector 26 and supports the radiation detector 26. As a result, it is possible to realize the simplification of the internal structure of the imaging table 24 as compared to a case in which a support structure that supports the protrusion 51A is separately provided inside the imaging table 24.

In addition, in a case in which the scattered ray removal grid is disposed as close to the detection surface 26A as possible, the effect of removing the scattered rays is higher. In a case in which a dedicated support structure that supports the protrusion 51A is separately provided, the dedicated support structure may be obstruction in a case in which the scattered ray removal grid is brought close to the detection surface 26A. The protrusion 51A is provided on the support member 54, and further protrudes along the normal direction of the detection surface 26A. As a result, the insertion grid 44 can be easily brought close to the radiation detector 26 as compared with a case in which the protrusion 51A is provided to be different from the installation position and the installation aspect in the present configuration.

Further, in the mammography apparatus 10 according to the second embodiment, the support member 54 is not provided on the chest wall side of the radiation detector 26 of the subject A. For this reason, the radiation detector 26 can be disposed closer to the chest wall side (that is, the front side). The insertion grid 44 is disposed at the facing position according to the position of the radiation detector 26. Therefore, the insertion grid 44 can also be brought closer to the chest wall side according to the position of the radiation detector 26. As a result, it is possible to expand an imaging range on the chest wall side in the mammography.

It should be noted that, in the second embodiment, the form example is described in which one protrusion 51A having a columnar shape is provided on each of the right side portion 54A and the left side portion 54B, but the technology of the present disclosure is not limited to this. The shape (for example, a hemispherical shape), the number, and the disposition location of the protrusions 51A can be appropriately set by the positioning accuracy of the insertion grid 44 or the like.

In addition, in the second embodiment, the form example is described in which the support member 54 supports the periphery of the detection surface 26A of the radiation detector 26 from three sides, but the technology of the present disclosure is not limited to this. For example, the support member 54 may have a frame shape that supports the entire periphery of the radiation detector 26, or may have an aspect in which only the rear side of the radiation detector 26 is supported.

Third Embodiment

In the first embodiment described above, the form example is described in which the insertion grid 44 is disposed at the facing position by the operation of the user, but the technology of the present disclosure is not limited to this. In the third embodiment, a guide part 56 that guides the insertion grid 44 to the facing position is provided inside the imaging table 24.

Figure 14:
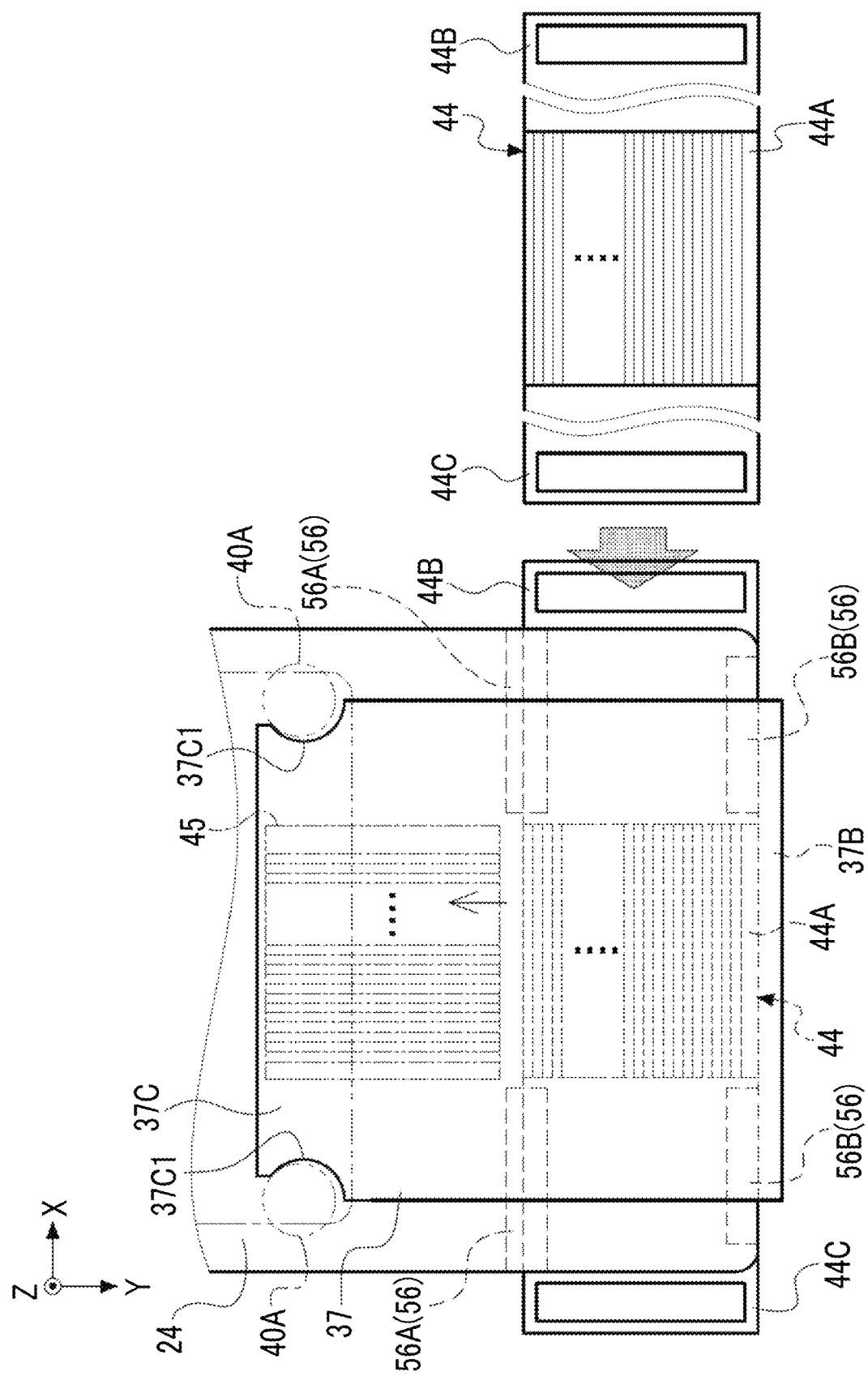
FIG. 14 is an exterior plan view showing an example of a state in which the insertion grid is guided by a guide part.

As shown in FIG. 14, the guide part 56 is provided inside the imaging table 24. The guide part 56 guides the insertion grid 44 to the facing position by engaging with the insertion grid 44. In the example shown in FIG. 14, the guide part 56 comprises guide rails 56A and 56B. The guide rails 56A and 56B are rail members that are disposed along the left-right direction inside the imaging table 24. The guide rail 56A supports the rear side of the insertion grid 44 in a case in which the insertion grid 44 is inserted into the imaging table 24. Further, the guide rail 56B supports the front side of the insertion grid 44 in a case in which the insertion grid 44 is inserted into the imaging table 24. The guide part 56 is an example of a "guide part" according to the technology of the present disclosure, and the guide rails 56A and 56B are examples of a "guide rail" according to the technology of the present disclosure.

The guide rails 56A and 56B do not engage with the grid body 44A in a case in which the insertion grid 44 is located at the facing position. Stated another way, the guide rails 56A and 56B are not provided in a detection range of the radiation.

Figure 15:
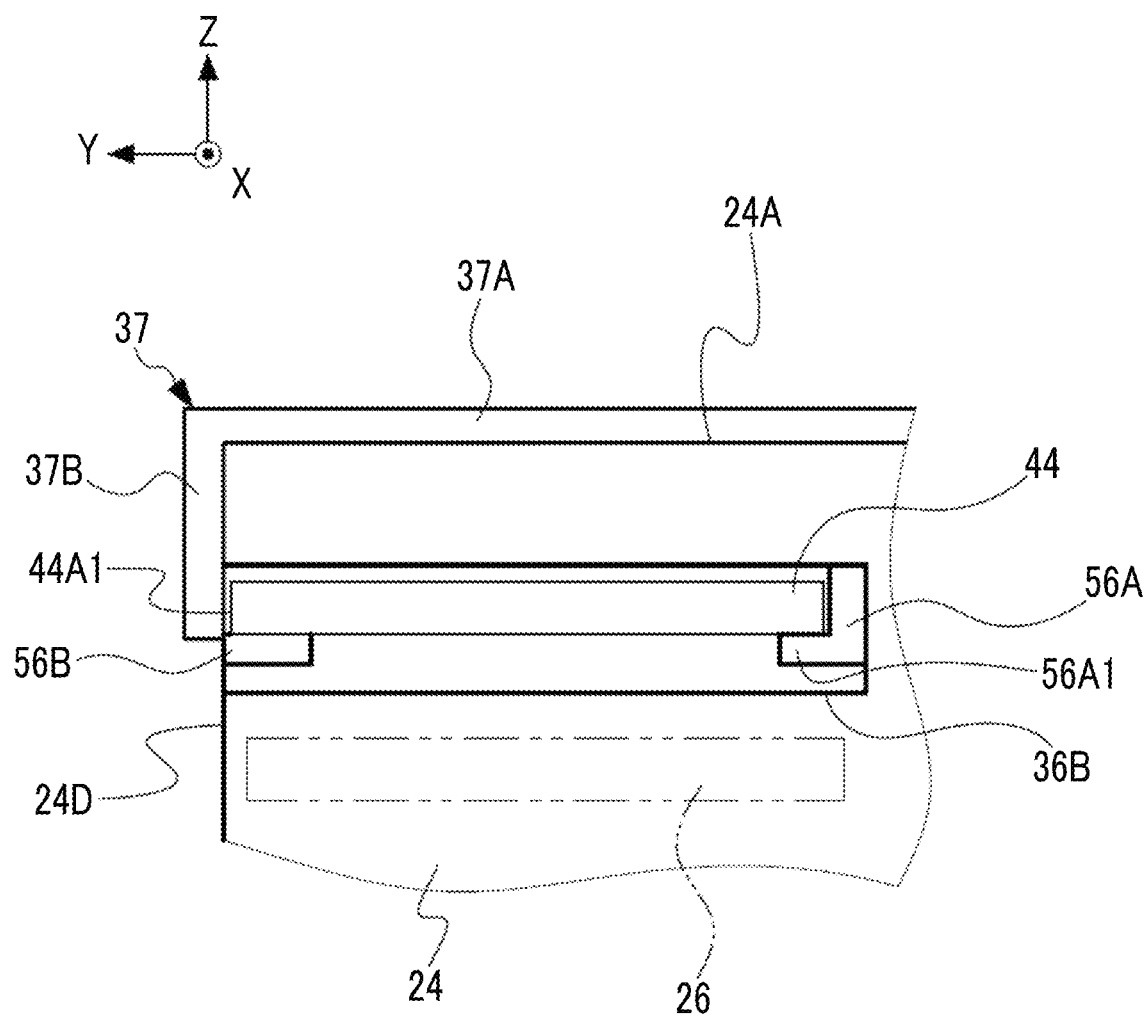
FIG. 15 is an exterior side view showing an example of a state in which the insertion grid is guided by the guide part.

As shown in FIG. 15, the guide rail 56A has an L-shape in a cross-sectional view (that is, the L-shape as viewed in the left-right direction). The guide rail 56A is attached to the interior wall on the rear side in the space K. One end portion 56A1 of the guide rail 56A supports the rear side of the insertion grid 44 from below. The guide rail 56B is a plate-shaped member, and is attached to the interior wall on the front side in the space K. The guide rail 56B supports the front side of the insertion grid 44 from below. As described above, the guide rails 56A and 56B can accept the insertion grid 44 from the left-right direction, and the insertion grid 44 is guided to the facing position by the guide rails 56A and 56B.

As described so far, in the mammography apparatus 10 according to the third embodiment, the guide part 56 that guides the insertion grid 44 inserted from the opening 36A to the facing position is provided inside the imaging table 24. By guiding the insertion grid 44 by the guide part 56, it is easier to perform the work of inserting or drawing out the insertion grid 44 into or from the imaging table 24.

In addition, for example, by guiding the insertion grid 44 by the guide part 56, it is suppressed that the insertion grid 44 comes into contact with the radiation detector 26. As a result, the damage to the detection surface 26A of the radiation detector 26 is suppressed.

In addition, in the mammography apparatus 10 according to the third embodiment, the guide part 56 includes the guide rails 56A and 56B that can accept the insertion grid 44 from the left-right direction. The guide rails 56A and 56B are provided outside the detection range of the radiation. As a result, it is suppressed that the guide rails 56A and 56B are included in the radiation image during the mammography.

It should be noted that, in the third embodiment described above, the form example is described in which the guide part 56 is the guide rails 56A and 56B, but the technology of the present disclosure is not limited to this. The guide part 56 need only be able to guide the insertion grid 44 to the facing position inside the imaging table 24, and may have, for example, a configuration in which the insertion grid 44 is guided by a plurality of rolls provided inside the imaging table 24.

In addition, in the third embodiment, the form example is described in which the guide rail 56A is the rail having the L-shape in the cross-sectional view and the guide rail 56B is the rail having the plate-shaped member, but the technology of the present disclosure is not limited to this. The shape, the length, and the disposition of the guide rails 56A and 56B are not also particularly limited, and the guide rails 56A and 56B need only be rails that can accept the insertion grid 44 from the left-right direction.

Fourth Embodiment

In the first embodiment, the form example is described in which the fixing mechanism 50 comprises the protrusion 51 provided inside the imaging table 24, and the recess part 44D provided in the insertion grid 44 and the protrusion 51 engage with each other, so that the insertion grid 44 is fixed inside the imaging table 24, but the technology of the present disclosure is not limited to this. In the fourth embodiment, a fixing mechanism 58 is provided outside the imaging table 24.

Figure 16:
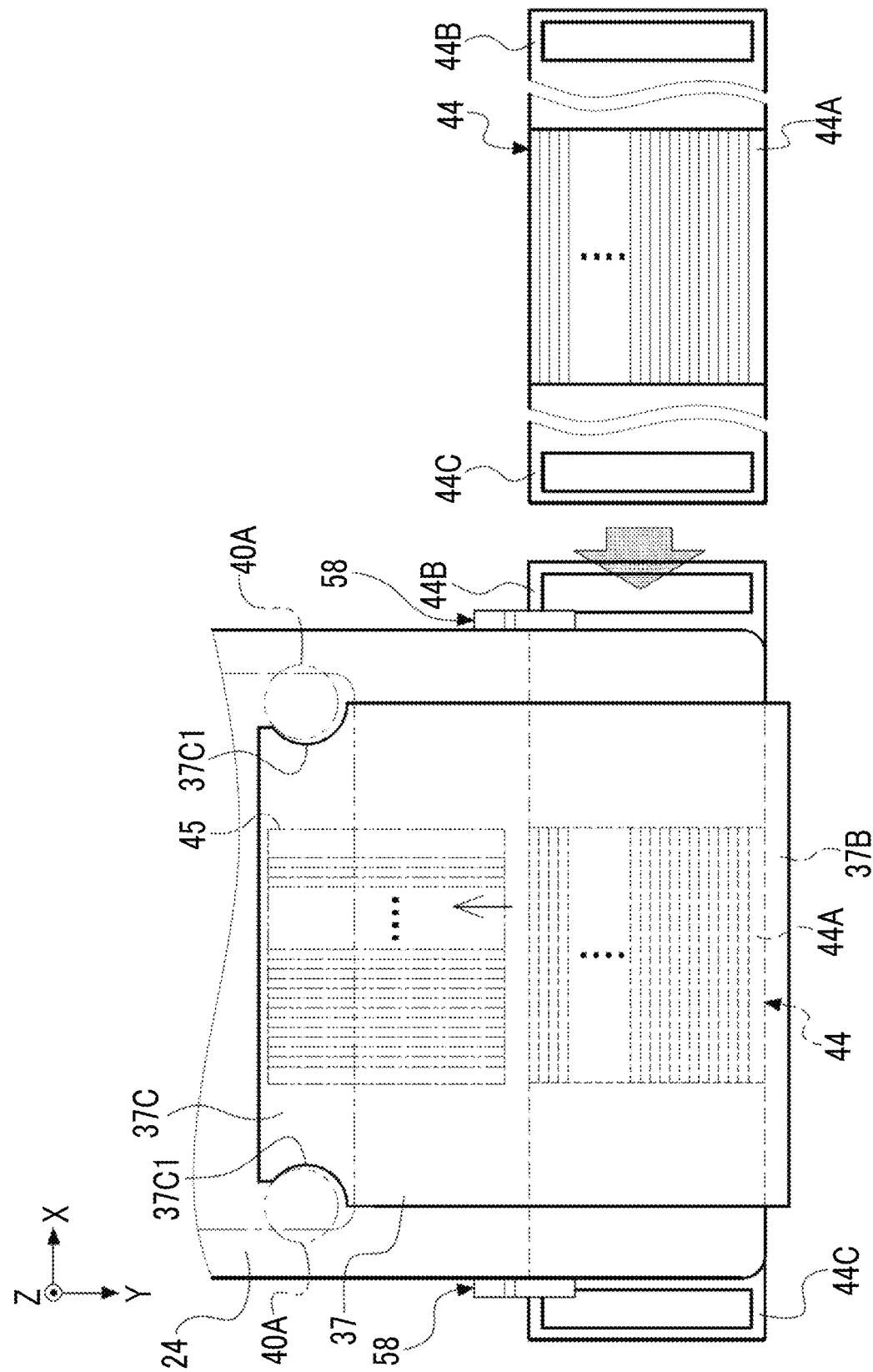
FIG. 16 is an exterior plan view showing still another example of the fixing mechanism.

As shown in FIG. 16, the fixing mechanism 58 fixes the insertion grid 44 at the facing position. The fixing mechanism 58 is provided outside the imaging table 24. Specifically, the fixing mechanism 58 is provided on the left side surface 24B and the right side surface 24C of the imaging table 24. The fixing mechanism 58 is an example of a "second fixing mechanism" according to the technology of the present disclosure.

Figure 17:
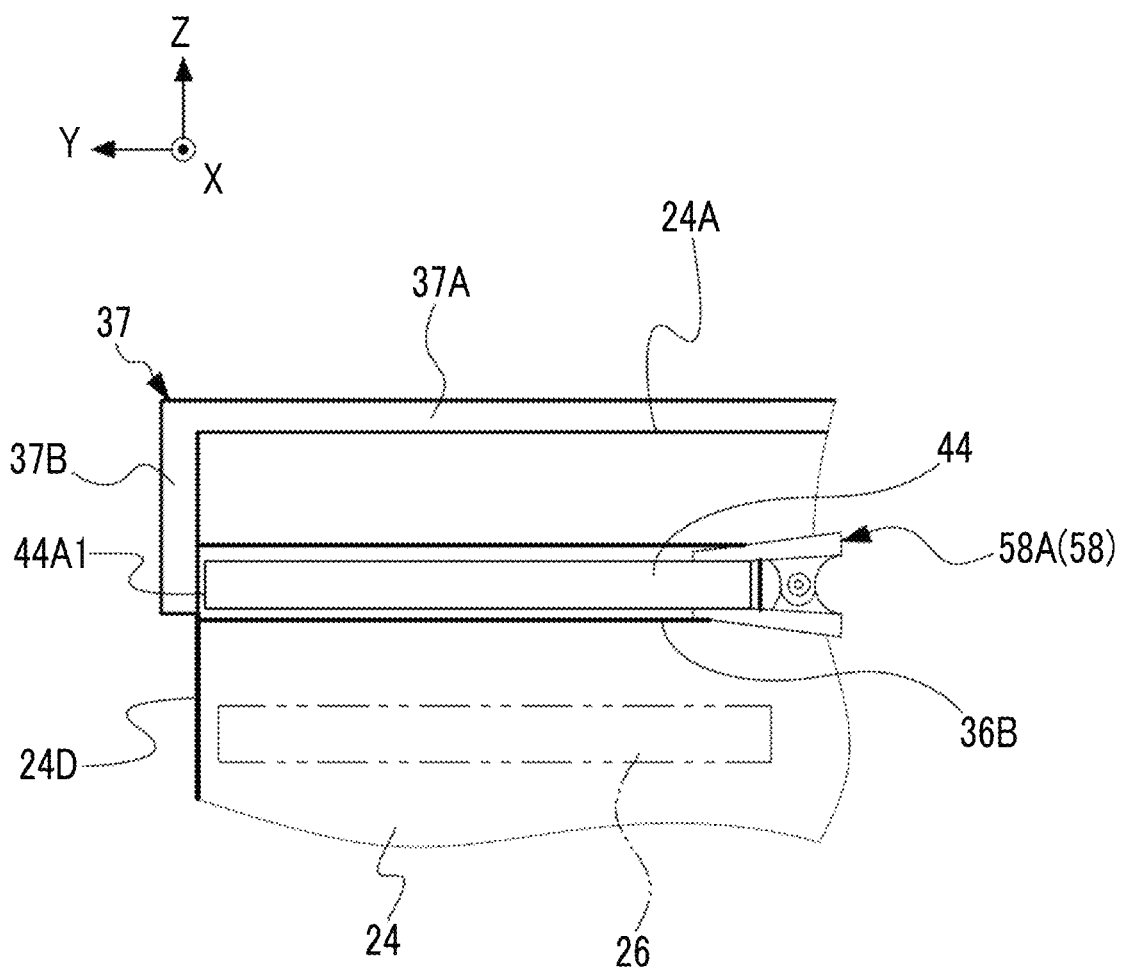
FIG. 17 is an exterior side view showing still another example of the fixing mechanism.

As shown in FIG. 17, the fixing mechanism 58 is a clip 58A. The clip 58A is provided on the side surface of the imaging table 24, and interposes a part of the insertion grid 44, which is exposed to the outside of the imaging table 24, in the up-down direction. Accordingly, the insertion grid 44 is fixed to the imaging table 24.

As described so far, in the mammography apparatus 10 according to the fourth embodiment, the insertion grid 44 is fixed inside the imaging table 24. The fixing mechanism 58 fixes the insertion grid 44 at the position facing the detection surface 26A of the radiation detector 26. Accordingly, the positioning accuracy of the insertion grid 44 is improved as compared with a case in which the insertion grid 44 is not fixed.

Further, for example, in the present configuration, the simplification of the internal structure of the imaging table 24 is realized as compared with a case in which the fixing mechanism 58 is provided inside the imaging table 24.

It should be noted that, in the fourth embodiment, the form example is described in which the fixing mechanism 58 is the clip 58A, but the technology of the present disclosure is not limited to this. The fixing mechanism 58 is not particularly limited as long as the fixing mechanism 58 has a configuration in which the insertion grid 44 can be fixed outside the imaging table 24, and for example, the insertion grid 44 may be adsorbed and fixed by a suction mechanism provided outside the imaging table 24. In addition, the insertion grid 44 may be fixed by attaching the magnet provided outside the imaging table 24 to the insertion grid 44 and magnetically attracting the magnet and the magnetizing plate to each other.

First Modification Example

In the first embodiment to the fourth embodiment described above, the form example is described in which the grip parts 44B and 44C remain extended along the left-right direction in a state in which the insertion grid 44 is inserted into the imaging table 24, but the technology of the present disclosure is not limited to this. In the first modification example, the grip parts 44B and 44C can be folded to a state of being along the vertical direction from a state of extending in the left-right direction.

Figure 18:
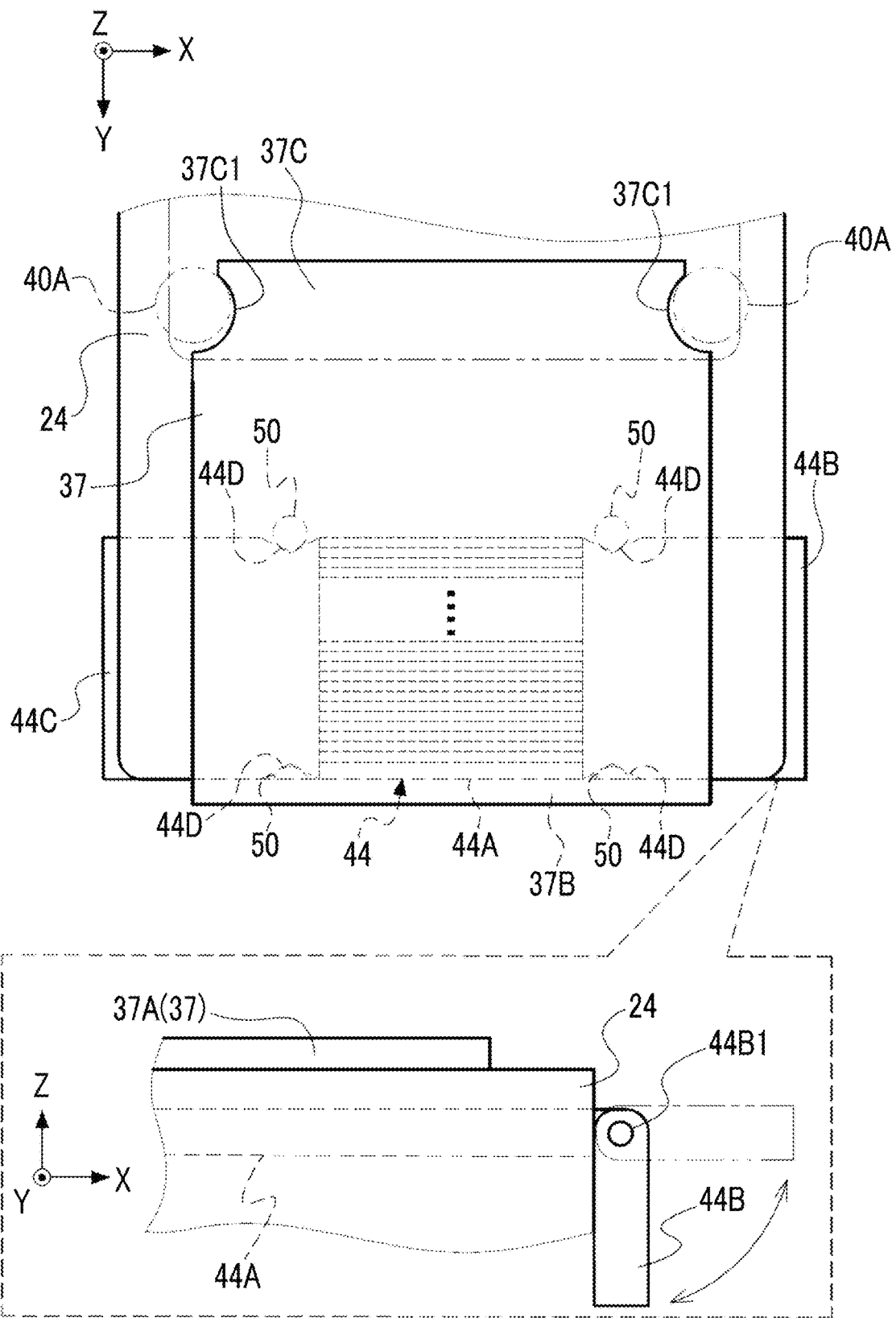
FIG. 18 is an exterior plan view showing another example of the insertion grid.

As shown in FIG. 18, the grip part 44B of the insertion grid 44 comprises a rotation shaft 44B1. The rotation shaft 44B1 is provided at a position closest to the imaging table 24 side in a part of the grip part 44B that protrudes from the imaging table 24. The rotation shaft 44B1 is a shaft member extending along the front-rear direction. A part of the grip part 44B that protrudes from the imaging table 24 is rotatable about the rotation shaft 44B1. The grip part 44B is in a state of extending in the left-right direction in a state in which the insertion grid 44 is inserted into the imaging table 24. Then, a part of the grip part 44B protruding from the imaging table 24 is rotated downward about the rotation shaft 44B1, and thus the grip part 44B is in a state of extending along the vertical direction. That is, the grip part 44B is folded. It should be noted that, although not shown, the grip part 44C is also provided with the same rotation mechanism as the grip part 44B, and the grip part 44C can be folded. It should be noted that the grip parts 44B and 44C may comprise a lock mechanism that regulates the rotation via the rotation shaft 44B1. As a result, the grip parts 44B and 44C are fixed in any one of a folded state or a state of extending in the left-right direction.

As described so far, in the first modification example, the grip part 44B can be folded. Therefore, even in a case in which the insertion grid 44 is inserted into the imaging table 24, it is suppressed that a part of the insertion grid 44 that protrudes from the imaging table 24 comes into contact with the outside (for example, the user, the subject, or the peripheral devices).

It should be noted that, in the first modification example, the form example is described in which the grip parts 44B and 44C can be folded, but the technology of the present disclosure is not limited to this. The grip parts 44B and 44C may be, for example, attachable to and detachable from the grid body 44A.

It should be noted that, in the embodiments described above, the form example is described in which the insertion grid 44 is inserted into the imaging table 24 and positioned by the operation of the user, but the technology of the present disclosure is not limited to this. A sensor provided inside the imaging table 24 may detect the position of the insertion grid 44 inside the imaging table 24. For example, a magnetic force sensor may be provided as the sensor, and may detect that the insertion grid 44 is located at the facing position by detecting the change in the magnetic field caused by the magnetic body attached to the insertion grid 44.

In addition, in the embodiments described above, a protective film may be formed on the detection surface 26A of the radiation detector 26. The protective film is generally made of a material having a high transmittance with respect to the radiation (for example, a carbon fiber reinforced resin). By forming the protective film on the detection surface 26A of the radiation detector 26, it is suppressed that the insertion grid 44 comes into direct contact with the detection surface 26A, and the damage of the detection surface 26A is suppressed.

Figure 19:
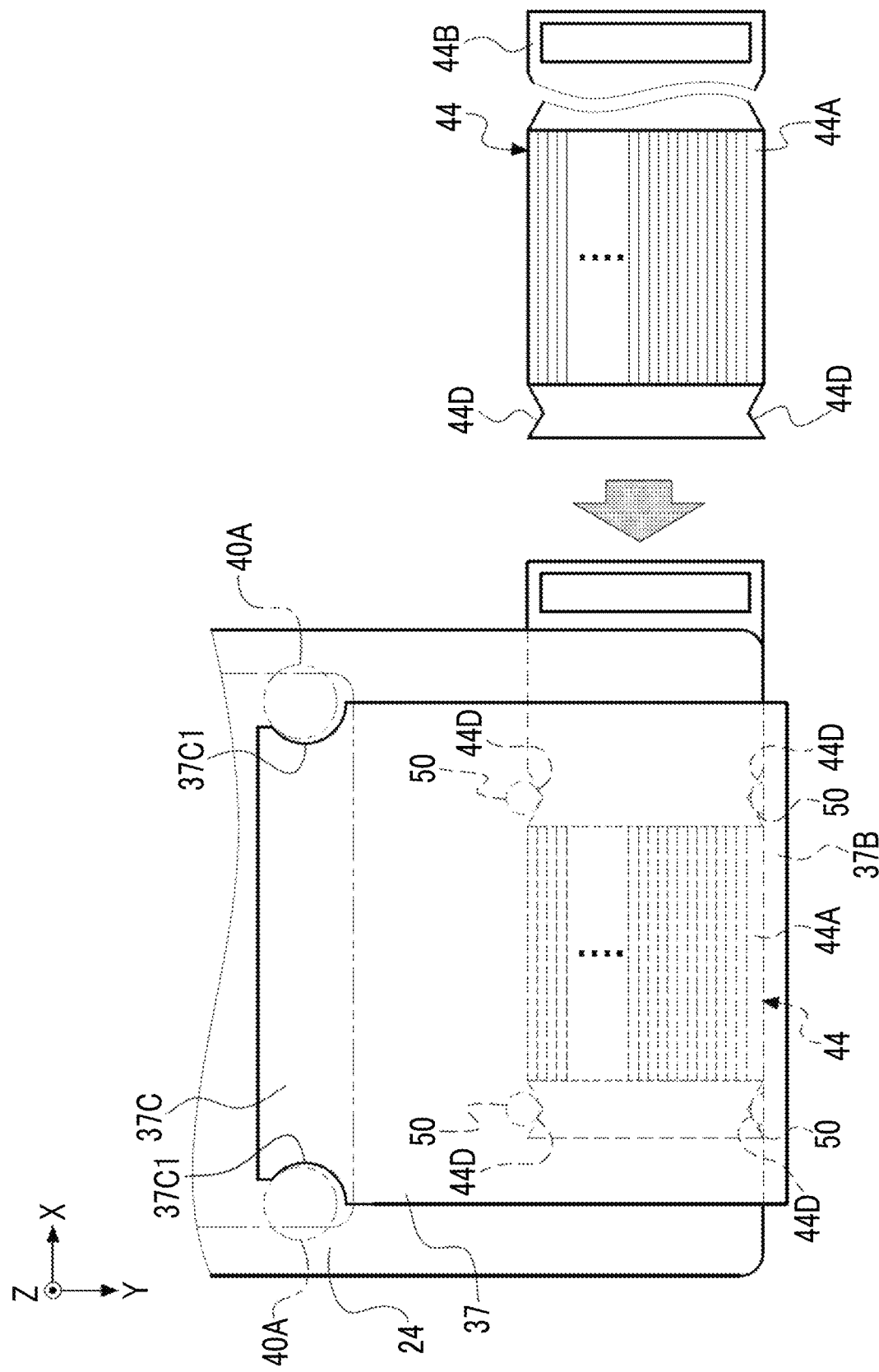
FIG. 19 is an exterior plan view showing still another example of the insertion grid.

In addition, in the embodiments described above, the form example is described in which the imaging table 24 has the openings 36A and 36B and the insertion grid 44 can be inserted from both sides of the imaging table 24 in the left-right direction, but the technology of the present disclosure is not limited to this. As shown in FIG. 19, the technology of the present disclosure is established even in a case in which the insertion grid 44 can be inserted only from one side (in the example shown in FIG. 19, the right side) of the imaging table 24 in the left-right direction.

In addition, in the embodiments described above, the form example is described in which the insertion grid 44 is inserted into the space K formed inside the imaging table 24 by retracting the built-in grid 45, but the technology of the present disclosure is not limited to this. For example, an aspect may be adopted in which the space K different from the space in which the built-in grid 45 is housed is formed inside the imaging table 24 and the insertion grid 44 is inserted into the space K.

It should be noted that, in the embodiments described above, the form example is described in which the imaging in which the stereo imaging and the contrast energy subtraction imaging are combined is performed, but the technology of the present disclosure is not limited to this. For example, a form may be adopted in which only the stereo imaging is performed.

In addition, in the embodiments described above, the form example is described in which the stereo imaging is performed by moving the radiation source 25 in the left-right direction, but the technology of the present disclosure is not limited to this. For example, the radiation source 25 may be a so-called multi-radiation source that comprises a plurality of tubes 25A arranged along the left-right direction and emits the radiation R from each tube 25A. In the multi-source, the plurality of tubes 25A are arranged in the left-right direction, so that the stereo imaging can be performed, for example, by using the tubes 25A at both ends in the left-right direction.

In addition, in the embodiments described above, the stereo imaging in a case in which the biopsy is performed is described, but the technology of the present disclosure is not limited to this. For example, the so-called tomosynthesis imaging, in which the breast M is imaged from a plurality of irradiation positions having different irradiation angles to obtain a tomographic image of the breast M, may be performed. Projection images of the breast M from the plurality of irradiation positions obtained by the tomosynthesis imaging are subjected to image reconstruction processing and used for generating the tomographic image of the breast M.

In addition, in the embodiments described above, the form example is described in which the radiography for the biopsy is performed, but the technology of the present disclosure is not limited to this. For example, the normal radiography without the biopsy may be performed. In such a case, the radiography is performed on the breast M placed on the imaging table 24 without using the biopsy unit 39 and the protective cover 37. For example, the insertion grid 44 has the same extending direction of the boundary line 48 as the built-in grid 45, but has a different grid density from the built-in grid 45. The user inserts the insertion grid 44 to perform the radiography under conditions of different grid densities.

In addition, in the embodiments described above, the form example is described in which one insertion grid 44 is prepared, but the technology of the present disclosure is not limited to this. For example, a plurality of insertion grids 44 having different grid densities may be prepared, and the plurality of insertion grids 44 may be replaced.

The described contents and the shown contents are the detailed description of the parts according to the technology of the present disclosure, and are merely examples of the technology of the present disclosure. For example, the description of the configuration, the function, the action, and the effect are the description of examples of the configuration, the function, the action, and the effect of the parts according to the technology of the present disclosure. Accordingly, it is needless to say that unnecessary parts may be deleted, new elements may be added, or replacements may be made with respect to the described contents and the shown contents within a range that does not deviate from the gist of the technology of the present disclosure. In addition, in order to avoid complications and facilitate understanding of the parts according to the technology of the present disclosure, the description of common technical knowledge or the like, which does not particularly require the description for enabling the implementation of the technology of the present disclosure, is omitted in the described contents and the shown contents.

All documents, patent applications, and technical standards described in the present specification are incorporated into the present specification by reference to the same extent as in a case in which the individual documents, patent applications, and technical standards are specifically and individually stated to be described by reference.

Regarding the embodiments described above, the following additional notes are further disclosed.

Additional Note 1

A mammography apparatus comprising an imaging table on which a breast of a subject is placed, which has an imaging surface on which radiation transmitted through the breast is incident, and in which a detector that detects the radiation transmitted through the imaging surface is housed, in which the imaging table is configured to attachably and detachably mount therein a scattered ray removal grid that removes scattered rays generated by the radiation transmitting through the breast, and in a case in which, in the imaging table, a direction connecting a chest wall side on which a chest wall of the subject is located and a side opposite to the chest wall is defined as a front-rear direction and a direction orthogonal to the front-rear direction is defined as a left-right direction, an opening for attaching and detaching the scattered ray removal grid is provided in the imaging table on at least any one of a left side surface or a right side surface of the imaging table.

Additional Note 2

The mammography apparatus according to additional note 1, in which the opening is provided on both the left side surface and the right side surface of the imaging table.

Additional Note 3

The mammography apparatus according to additional note 1 or 2, in which the scattered ray removal grid is a grid in which a plurality of transmission parts that transmit the radiation and a plurality of absorption parts that absorb the radiation are alternately arranged and a boundary line between the transmission part and the absorption part extends in one direction, and the scattered ray removal grid is able to be disposed inside the imaging table in a posture in which the direction in which the boundary line extends is parallel to the left-right direction.

Additional Note 4

The mammography apparatus according to any one of additional notes 1 to 3, in which a first fixing mechanism that fixes the scattered ray removal grid at a facing position facing a detection surface of the detector is provided inside the imaging table.

Additional Note 5

The mammography apparatus according to additional note 4, in which the first fixing mechanism includes a protrusion that is able to engage with a recess part provided in the scattered ray removal grid.

Additional Note 6

The mammography apparatus according to additional note 5, in which a support member that supports the detector and is disposed on at least a part of a periphery of the detection surface is provided inside the imaging table, and the protrusion is provided on the support member to protrude along a normal direction of the detection surface.

Additional Note 7

The mammography apparatus according to additional note 6, in which the support member is not provided on the chest wall side of the detector.

Additional Note 8

The mammography apparatus according to any one of additional notes 1 to 7, in which a guide part that guides the scattered ray removal grid to a facing position facing a detection surface of the detector by engaging with the scattered ray removal grid inserted from the opening is provided inside the imaging table.

Additional Note 9

The mammography apparatus according to additional note 8, in which the guide part is a guide rail that is able to accept the scattered ray removal grid from the left-right direction, and the guide rail is provided outside a detection range of the radiation in the front-rear direction and the left-right direction.

Additional Note 10

The mammography apparatus according to any one of additional notes 1 to 9, in which a second fixing mechanism that fixes the scattered ray removal grid at a facing position facing a detection surface of the detector and is provided outside the imaging table is provided.

Additional Note 11

The mammography apparatus according to any one of additional notes 1 to 10, in which the scattered ray removal grid is provided with a grip member.

Additional Note 12

The mammography apparatus according to any one of additional notes 1 to 11, in which, in a case in which the scattered ray removal grid is an external grid, a built-in grid that is built in the imaging table is provided in the imaging table as a scattered ray removal grid different from the external grid, the built-in grid is movable in the imaging table between a facing position facing a detection surface of the detector and a retreat position retreating from the facing position, and the external grid is inserted into the imaging table in a state in which the built-in grid is moved to the retreat position.

What is claimed is:

1. A mammography apparatus comprising:
an imaging table on which a breast of a subject is placed, which has an imaging surface on which radiation transmitted through the breast is incident, and in which a detector that detects the radiation transmitted through the imaging surface is housed,
wherein the imaging table is configured to attachably and detachably mount therein a scattered ray removal grid that removes scattered rays generated by the radiation transmitting through the breast, and
in a case in which, in the imaging table, a direction connecting a chest wall side on which a chest wall of the subject is located and a side opposite to the chest wall is defined as a front-rear direction and a direction orthogonal to the front-rear direction is defined as a left-right direction, an opening for attaching and detaching the scattered ray removal grid is provided in the imaging table on at least any one of a left side surface or a right side surface of the imaging table.

2. The mammography apparatus according to claim 1, wherein the opening is provided on both the left side surface and the right side surface of the imaging table.

3. The mammography apparatus according to claim 1, wherein the scattered ray removal grid is a grid in which a plurality of transmission parts that transmit the radiation and a plurality of absorption parts that absorb the radiation are alternately arranged and a boundary line between the transmission part and the absorption part extends in one direction, and
the scattered ray removal grid is able to be disposed inside the imaging table in a posture in which the direction in which the boundary line extends is parallel to the left-right direction.

4. The mammography apparatus according to claim 1, wherein a first fixing mechanism that fixes the scattered ray removal grid at a facing position facing a detection surface of the detector is provided inside the imaging table.

5. The mammography apparatus according to claim 4, wherein the first fixing mechanism includes a protrusion that is able to engage with a recess part provided in the scattered ray removal grid.

6. The mammography apparatus according to claim 5, wherein a support member that supports the detector and is disposed on at least a part of a periphery of the detection surface is provided inside the imaging table, and
the protrusion is provided on the support member to protrude along a normal direction of the detection surface.

7. The mammography apparatus according to claim 6, wherein the support member is not provided on the chest wall side of the detector.

8. The mammography apparatus according to claim 1,
wherein a guide part that guides the scattered ray removal grid to a facing position facing a detection surface of the detector by engaging with the scattered ray removal grid inserted from the opening is provided inside the imaging table.

9. The mammography apparatus according to claim 8,
wherein the guide part is a guide rail that is able to accept the scattered ray removal grid from the left-right direction, and
the guide rail is provided outside a detection range of the radiation in the front-rear direction and the left-right direction.

10. The mammography apparatus according to claim 1,
wherein a second fixing mechanism that fixes the scattered ray removal grid at a facing position facing a detection surface of the detector and is provided outside the imaging table is provided.

11. The mammography apparatus according to claim 1,
wherein the scattered ray removal grid is provided with a grip member.

12. The mammography apparatus according to claim 1,
wherein, in a case in which the scattered ray removal grid is an external grid, a built-in grid that is built in the imaging table is provided in the imaging table as a scattered ray removal grid different from the external grid,
the built-in grid is movable in the imaging table between a facing position facing a detection surface of the detector and a retreat position retreating from the facing position, and
the external grid is inserted into the imaging table in a state in which the built-in grid is moved to the retreat position.

* * * * *